US012227566B2

United States Patent
Jung et al.

(10) Patent No.: US 12,227,566 B2
(45) Date of Patent: Feb. 18, 2025

(54) ENDOTHELIN RECEPTOR TYPE A ACTIVITY REGULATING ANTIBODY

(71) Applicant: HEDGEHOG, INC., Seoul (KR)

(72) Inventors: Sang Taek Jung, Gyeonggi-do (KR); Yeon Gyu Yu, Seoul (KR); Man-Seok Ju, Gyeonggi-do (KR); Jung-Hyun Na, Seoul (KR); Youn Jae Kim, Seoul (KR); Hye-Mi Ahn, Gyeonggi-do (KR); Byoung Joon Ko, Chungcheongbuk-do (KR); Won Kyu Lee, Gyeonggi-do (KR)

(73) Assignee: HEDGEHOG, INC., Seoul (KR)

( * ) Notice: Subject to any disclaimer, the term of this patent is extended or adjusted under 35 U.S.C. 154(b) by 872 days.

(21) Appl. No.: 17/311,537

(22) PCT Filed: Dec. 5, 2019

(86) PCT No.: PCT/KR2019/017110
§ 371 (c)(1),
(2) Date: Jun. 7, 2021

(87) PCT Pub. No.: WO2020/116963
PCT Pub. Date: Jun. 11, 2020

(65) Prior Publication Data
US 2022/0153831 A1    May 19, 2022

(30) Foreign Application Priority Data

Dec. 5, 2018 (KR) .................. 10-2018-0155319
Dec. 4, 2019 (KR) .................. 10-2019-0159941

(51) Int. Cl.
C07K 16/28       (2006.01)
A61K 39/00       (2006.01)
A61P 35/00       (2006.01)

(52) U.S. Cl.
CPC .............. *C07K 16/28* (2013.01); *A61P 35/00* (2018.01); *A61K 2039/505* (2013.01); *C07K 2317/56* (2013.01); *C07K 2317/565* (2013.01); *C07K 2317/76* (2013.01)

(58) Field of Classification Search
CPC ............... C07K 16/28; C07K 2317/56; C07K 2317/565; C07K 2317/73; C07K 2317/76; C07K 2317/92; C07K 16/2869; A61P 35/00; A61P 9/12; A61K 2039/505
See application file for complete search history.

(56) References Cited

U.S. PATENT DOCUMENTS

| 9,644,038 B2 | 5/2017 | Luo |
| 10,568,947 B2 | 2/2020 | Brogdon et al. |
| 2004/0014194 A1 | 1/2004 | Beyer |
| 2012/0100140 A1 | 4/2012 | Reyes |
| 2018/0256714 A1 | 9/2018 | Zhang |
| 2022/0235140 A1 | 7/2022 | Jung |

FOREIGN PATENT DOCUMENTS

| CN | 107987162 | 5/2018 |
| JP | 2008-280266 | 11/2008 |
| JP | 2010-138165 | 6/2010 |
| KR | 1020090113904 | 11/2009 |
| KR | 1020180113904 | 10/2018 |
| KR | 20180136327 | 12/2018 |
| WO | 2012045776 | 4/2012 |

OTHER PUBLICATIONS

Mai H., et al., "Correlation of endothelin A receptor expression to prognosis of nasopharyngeal carcinoma," Ai Zheng. May 2005;24(5):611-5. Chinese. PMID: 15890108.
Ju, M.S., et al., "A human antibody against human endothelin receptor type A that exhibits antitumor potency," Experimental & Molecular Medicine (2021) 53:1437-1448.
Ju, M.S., et al., "P0230 isolation of Human Anti-GPCR Antibodies Using Nanodisc Proteins," Integrated Biotechnology for Human Well-Being, 2017 KSBB Spring Meeting and International Symposium, Hwebeek International Convention Center, Gyeongju, Apr. 5-7, 2017.
NCBI, GenBank accession No. XP_008967127.1, May 1, 2018.
Lee, K., et al., "Purification and characterization of recombinant human endothelin receptor type A," Protein Expression and Purification 84 (2012) 14-18.
Jo, M., et al., "Engineering therapeutic antibodies targeting G-protein-coupled receptors," Experimental & Molecular Medicine (2016) 48.
Lappano, R., et al., "G protein-coupled receptors: novel targets for drug discovery in cancer," Nature Reviews, Drug Discovery, vol. 10, Jan. 2011, pp. 47-60.
Rosano, L., et al., "Endothelin 1 in cancer: biological implications and therapeutic opportunities," Nature Reviews, Cancer, vol. 13, Sep. 2013, pp. 637-651.

*Primary Examiner* — Brad Duffy
*Assistant Examiner* — Carol Ann Chase
(74) *Attorney, Agent, or Firm* — DUANE MORRIS LLP; Gregory M. Lefkowitz; Brandon A. Chan

(57) ABSTRACT

The present invention relates to a monoclonal antibody or a fragment thereof that recognizes and binds specifically to the extracellular domain of endothelin receptor type A as an antigen. The monoclonal antibody of the present invention is suitable for use in a therapeutic agent for hypertension or cancer associated with endothelin receptor type A.

17 Claims, 15 Drawing Sheets
Specification includes a Sequence Listing.

| Glycan ID | Percent of total intensity(%) | | | | | |
|---|---|---|---|---|---|---|
| | IgG(Standard) | FG12 | AB9 | AG8 | EF12 | GG12 |
| G0 | 1.65 | - | - | - | - | - |
| G0F | 46.01 | 62.32 | 61.42 | 58.81 | 60.65 | 63.25 |
| G1 | 1.23 | 14.68 | 12.61 | 14.93 | 12.10 | 13.97 |
| G1F_1 | 20.23 | 14.13 | 15.75 | 16.01 | 13.91 | 14.28 |
| G1F_2 | 22.15 | 6.47 | 7.58 | 7.31 | 7.02 | 6.52 |
| G2F | 8.74 | 2.40 | 2.63 | 2.93 | 5.03 | 1.98 |
| Unknown at 19.81 | - | - | - | - | 1.29 | - |

| sample | | Theoretical mass (full seq.) | Observed mass | Δ mass (Obs-Theo) | N-glcan (G0F/G0F) | C-term (-2K) | N-term (Glu->Gln) | Δ mass (Δ mass-(2G0F-2K)) |
|---|---|---|---|---|---|---|---|---|
| Native | FG12 | 145818.14 | 148430.00 | 2611.86 | 2890 | 256.344 | 17 | -4.80 |
| | AB9 | 145729.84 | 148343.80 | 2613.96 | 2890 | 256.344 | 17 | -2.70 |
| | AG8 | 145765.96 | 148382.30 | 2616.34 | 2890 | 256.344 | 17 | -0.32 |
| | EF12 | 145647.82 | 148261.20 | 2613.38 | 2890 | 256.344 | 17 | -3.28 |
| | GG12 | 145762.02 | 148376.60 | 2614.58 | 2890 | 256.344 | 17 | -2.08 |
| PNGaseF | FG12 | 145818.14 | 145543.20 | -274.94 | 0.00 | 256.344 | 17 | -1.60 |
| | AB9 | 145729.84 | 145455.50 | -274.34 | 0.00 | 256.344 | 17 | -1.00 |
| | AG8 | 145765.96 | 145492.50 | -273.46 | 0.00 | 256.344 | 17 | -0.12 |
| | EF12 | 145647.82 | 145373.90 | -273.92 | 0.00 | 256.344 | 17 | -0.58 |
| | GG12 | 145762.02 | 145486.20 | -275.82 | 0.00 | 256.344 | 17 | -2.48 |

ENDOTHELIN RECEPTOR TYPE A ACTIVITY REGULATING ANTIBODY

CROSS-REFERENCE TO RELATED APPLICATIONS

This application is a § 371 national stage entry of International Application No. PCT/KR2019/017110, filed on Dec. 5, 2019, which claims priority to Korean Patent Application No. 10-2018-0155319, filed on Dec. 5, 2018 and Korean Patent Application No. 10-2019-0159941, filed on Dec. 4, 2019, the entire contents of which are incorporated herein by reference.

TECHNICAL FIELD

The present invention relates to an antibody that effectively inhibits binding between endothelin-1 (ET-1) and endothelin receptor type A ($ET_A$) to modulate the activity of $ET_A$ due to its enhanced binding to $ET_A$.

SEQUENCE LISTING

The instant application contains a Sequence Listing which has been submitted electronically and is hereby incorporated by reference in its entirety. Said ASCII file was created on Sep. 24, 2024, is named G1035-19701_ST25, and is 58,495 bytes in size.

BACKGROUND ART

G-protein coupled receptors (GPCRs) are multi-transmembrane proteins with seven transmembrane domains. GPCRs can transduce extracellular signals to the interior of cells to activate G-protein heterotrimers. Due to their ability, GPCRs play physiologically essential roles in senses as well as responses to neurotransmitters. In addition, GPCRs not only directly regulate major biological processes (including cell growth, proliferation, migration, clustering, and death) at the highest level, but also are directly associated with diseases such as cancer and cardiovascular diseases. For these reasons, GPCRs have attracted attention as major drug targets.

It is known that endothelin receptor type A ($ET_A$) is expressed mainly in the vascular smooth muscle of normal humans and causes vasoconstriction through intracellular signaling pathways when bound to its ligand, endothelin-1 (ET-1). On the other hand, drugs such as bosentan, an endothelin receptor antagonist, have been used as therapeutic agents for hypertension (Nature reviews drug discovery, 2011, Vol. 10, 47). Many recent basic biological and clinical studies have reported that $ET_A$ is overexpressed in various cancers such as bladder cancer, lung cancer, ovarian cancer, kidney cancer, colorectal cancer, prostate cancer, breast cancer, uterine cancer, rhabdomyosarcoma, and glioblastoma and is directly involved in main cancer processes such as proliferation, migration, invasion, metastasis, and angiogenesis of cancer cells to lower the survival rate of patients. Thus, $ET_A$ has been spotlighted as major anticancer targets (Nature review cancer, 2013, Vol. 13, 637).

Antibody drugs have many advantages such as high specificity, few side effects, long blood half-life, and multiple mechanisms of action to kill defective cells (ADCC, ADCP, and CDC) by their Fc regions compared to synthetic small-molecule drugs. Nevertheless, current $ET_A$-targeted drugs are small-molecule drugs, including bosentan, zibotentan, and atrasentan, and no satisfactory antibody drugs have been reported as yet. Only a very few antibody drugs have been approved for sale even if extended to all GPCRs.

Poteligeo (Mogamulizumab) available from Kyowa Hakko Kirin is a CCR4-targeted antibody approved in Japan. Aimovig (Erenumab) developed by Amgen in May, 2018 targets CGRP receptors and is the first U.S. FDA-approved GPCR-targeted antibody. Under these circumstances, there arises a need to develop a novel antibody that specifically binds to $ET_A$ and modulates the activity of $ET_A$. Specific binding to the extracellular domain (ECD) of an antigen is a prerequisite for the development of a novel GPCR-targeted antibody drug. However, considering that the extracellular domain accounts for a very limited proportion (~10%) of the entire surface area of GPCR, conventional strategies for antibody development are limited in their application.

The description of the Background Art is merely provided for better understanding the background of the invention and should not be taken as corresponding to the prior art already known to those skilled in the art.

DETAILED DESCRIPTION OF THE INVENTION

Problems to be Solved by the Invention

The inventors of the present invention have earnestly and intensively conducted research to develop a novel antibody that specifically binds to $ET_A$ to inhibit signal transduction pathways, and as a result, found an antibody that effectively inhibits ET-1 signaling in a cell line stably expressing $ET_A$. Based on this finding, the present invention has been accomplished.

Therefore, one object of the present invention is to provide a monoclonal antibody or a fragment thereof that recognizes and binds specifically to endothelin receptor type A or its extracellular domain as an antigen.

A further object of the present invention is to provide a nucleic acid molecule encoding the monoclonal antibody or fragment thereof.

Another object of the present invention is to provide a vector including the nucleic acid molecule.

Another object of the present invention is to provide a host cell including the vector.

Another object of the present invention is to provide a pharmaceutical composition for preventing or treating cancer or hypertension including the monoclonal antibody, the nucleic acid molecule or the vector.

Another object of the present invention is to provide a method for treating cancer or hypertension including administering to a subject a pharmaceutically effective amount of the monoclonal antibody, the nucleic acid molecule or the vector.

Another object of the present invention is to provide use of the monoclonal antibody or fragment thereof, the nucleic acid molecule or the vector in the preparation of a pharmaceutical composition for treating cancer or hypertension.

Another object of the present invention is to provide a method for quantifying endothelin receptor type A in a sample, including treating the sample with the monoclonal antibody or fragment thereof.

Another object of the present invention is to provide a method for providing information necessary for the diagnosis of a disease caused by overexpression of endothelin receptor type A.

Still another object of the present invention is to provide a kit for quantifying endothelin receptor type A including the monoclonal antibody or fragment thereof.

Other objects and advantages of the invention become more apparent from the following detailed description, claims, and drawings.

Means for Solving the Problems

One aspect of the present invention provides a monoclonal antibody or a fragment thereof that recognizes and binds specifically to endothelin receptor type A or its extracellular domain as an antigen.

The endothelin receptor type A is responsible for intracellular signaling when bound to its ligand, endothelin-1 (ET-1), and has received attention as a major target for hypertension treatment and anticancer therapy. Current $ET_A$-targeted drugs are low molecular weight compounds, including bosentan, zibotentan, and atrasentan, and there have been no reports on monoclonal antibody drugs that recognize the extracellular domain of endothelin receptor type A as an antigen.

As used herein, the term "antigen" refers to any natural or synthetic immunogenic substance, such as a protein, peptide, or hapten. An antigen can be $ET_A$ or a fragment thereof.

An "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). Epitopes formed from contiguous amino acids are typically, but not always, retained on exposure to denaturing solvents, whereas epitopes formed by tertiary folding are typically lost on treatment with denaturing solvents. An epitope typically includes at least 1, 2, 3, 4, 5, 6, 7, 8, 9, 10, 11, 12, 13, 14, 15, or 20 amino acids in a unique spatial conformation. Methods for determining what epitopes are bound by a given antibody (i.e., epitope mapping) are known in the art and include, for example, immunoblotting and immunoprecipitation assays, wherein overlapping or contiguous peptides from (e.g., from $ET_A$) are tested for reactivity with a given antibody (e.g., anti-$ET_A$ antibody). Methods of determining spatial conformation of epitopes include techniques in the art and those described herein, for example, x-ray crystallography, 2-dimensional nuclear magnetic resonance and FIDX-MS (see, e.g., Epitope Mapping Protocols in Methods in Molecular Biology, Vol. 66, G. E. Morris, Ed. (1996)).

In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al., (1994) *Acta Crystallogr D Biol Crystallogr* 50(Pt 4): 339-350; McPherson A (1990) *Eur J Biochem* 189: 1-23; Chayen E (1997) *Structure* 5: 1269-1274; McPherson A (1976) *J Biol Chem* 251:6300-6303). Antibody:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al., (2000) *Acta Crystallogr D Biol Crystallogr* 56(Pt 10): 1316-1323). Mutagenesis mapping studies can be accomplished using any method known to one of skill in the art. See, e.g., Champe M et al., (1995) *J Biol Chem* 270: 1388-1394 and Cunningham B C & Wells J A (1989) *Science* 244: 1081-1085 for a description of mutagenesis techniques, including alanine scanning mutagenesis techniques.

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on $ET_A$" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition can be different depending on which antibody is the "blocking antibody" (i.e., the cold antibody that is incubated first with the target). Competition assays can be conducted as described, e.g., in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

A "bispecific" or "bifunctional antibody" is an artificial hybrid antibody having two different heavy/light chain pairs and two different binding sites. Bispecific antibodies can be produced by variety of methods including fusion of hybridomas or linking of Fab' fragments. See, e.g., Songsivilai & Lachmann, Clin. Exp. Immunol. 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) *Nature* Biotech. 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

The term "cross-reacts," as used herein, refers to the ability of an antibody described herein to bind to $ET_A$ from a different species. For example, an antibody described herein that binds human $ET_A$ can also bind another species of $ET_A$ (e.g., mouse $ET_A$). As used herein, cross-reactivity can be measured by detecting a specific reactivity with purified antigen in binding assays (e.g., SPR, ELISA) or binding to, or otherwise functionally interacting with, cells physiologically expressing $ET_A$. Methods for determining cross-reactivity include standard binding assays as described herein, for example, by BIACORE surface plasmon resonance (SPR) analysis using a BIACORE 2000 SPR instrument (Biacore AB, Uppsala, Sweden), or flow cytometric techniques.

The antibody or fragment thereof of the present invention recognizes and specifically binds to the extracellular domain of a GPCR (e.g., endothelin receptor type A) as an antigen wherein the extracellular domain of the GPCR includes one N-term and three ECLs (ECL1, ECL2, and ECL3). That is, the antibody or fragment thereof of the present invention can bind specifically to at least one domain selected from the group consisting of N-term, ECL1, ECL2, and ECL3 as an epitope. The epitope may include one or more amino acids.

According to a preferred embodiment of the present invention, the endothelin receptor type A includes the amino acid sequence of SEQ ID NO: 68.

According to a preferred embodiment of the present invention, the extracellular domain includes one or more domains selected from the group consisting of N-term of SEQ ID NO: 69, ECL1 of SEQ ID NO: 70, ECL2 of SEQ ID NO: 71, and ECL3 of SEQ ID NO: 72.

Antibodies can be of any type (e.g., IgG, IgE, IgM, IgD, IgA, or IgY) or any subclass (e.g., IgG1, IgG2, IgG3, and IgG4 in humans; and IgG1, IgG2a, IgG2b, and IgG3 in mice) of immunoglobulin molecule. Immunoglobulins, e.g., IgG1, exist in several allotypes. The term "antibody" as used herein is intended to include commonly known isotypes and allotypes. The antibodies described herein are of the IgG1, IgG2, IgG3, or IgG4 subclass or any hybrid thereof (e.g., a hybrid of IgG2 and IgG4).

The term "monoclonal antibody," as used herein, refers to an antibody that displays a single binding specificity and affinity for a particular epitope.

The term "fragment" as used herein refers to one or more fragments of an antibody that retain the ability to specifically bind to an antigen. Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding fragment" of an antibody, e.g., anti-$ET_A$ described herein, include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and disulfide-linked Fvs (sdFv); (v) a dAb fragment (Ward et al., (1989) *Nature* 341:544-546), which consists of a VH domain; and (vi) an isolated complementarity determining region (CDR) or (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see, e.g., Bird et al., (1988) *Science* 242:423-426; and Huston et al., (1988) *Proc. Natl. Acad. Sci. USA* 85:5879-5883. Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antigen-binding fragments can be produced by recombinant DNA techniques, or by enzymatic or chemical cleavage of intact immunoglobulins.

A VH domain, or one or more CDRs thereof, described herein can be linked to a constant domain for forming a heavy chain. Similarly, a VL domain, or one or more CDRs thereof, described herein can be linked to a constant domain for forming a light chain. A full length heavy chain and full length light chain combine to form a full length antibody.

As used herein, the terms "variable region" and "variable domain" are used interchangeably. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are specialized in the binding and specificity of a particular antibody for its particular antigen. The variability in sequence is concentrated in those regions (heavy chain: HCDR1, 2, and 3, light chain: LCDR1, 2, and 3) called complementarity determining regions (CDRs) while the more highly conserved regions in the variable domain are called framework regions (FR).

The CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In certain embodiments, the variable region is a primate (e.g., non-human primate) variable region. In certain embodiments, the variable region comprises rodent or murine CDRs and primate (e.g., non-human primate) framework regions (FRs).

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to any distinct type, e.g., kappa (κ) or lambda (k) based on the amino acid sequence of the constant domains. Light chain amino acid sequences are well known in the art. In specific embodiments, the light chain is a human light chain.

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, a Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains C 2 and C 3 and the hinge between C 1 and C 2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The CH2 domain of a human IgG Fc region extends from about amino acid 231 to about amino acid 340, whereas the CH3 domain is positioned on C-terminal side of a Cm domain in a Fc region, i.e., it extends from about amino acid 341 to about amino acid 447 of an IgG. As used herein, the Fc region can be a native sequence Fc, including any allotypic variant, or a variant Fc (e.g., a non-naturally-occurring Fc). Fc can also refer to a Fc-comprising protein polypeptide such as a "binding protein comprising a Fc region," also referred to as an "Fc fusion protein" (e.g., an antibody or immunoadhesion).

A "native sequence Fc region" or "native sequence Fc" comprises an amino acid sequence that is identical to the amino acid sequence of a Fc region found in nature. Native sequence human Fc regions include a native sequence human IgG1 Fc region; native sequence human IgG2 Fc region; native sequence human IgG3 Fc region; and native sequence human IgG4 Fc region as well as naturally-occurring variants thereof. Native sequence Fc includes the various allotypes of Fcs (see, e.g., Jefferis et al., (2009) mAbs 1:1; Vidarsson G. et al. Front Immunol. 5:520).

The constant region can be manipulated, e.g., by recombinant technology, to eliminate one or more effector functions. An "effector function" refers to the interaction of an antibody Fc region with a Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with a binding domain (e.g., an antibody variable domain). Accordingly, the term "a constant region without the Fc function" include constant regions with reduced or without one or more effector functions mediated by Fc region.

Effector functions of an antibody can be reduced or avoided by different approaches. Effector functions of an antibody can be reduced or avoided by using antibody fragments lacking the Fc region (e.g., such as a Fab, F(ab')2, single chain Fv (scFv), or a sdAb consisting of a monomeric VH or VL domain). Alternatively, the so-called aglycosylated antibodies can be generated by removing sugars that are linked to particular residues in the Fc region to reduce the effector functions of an antibody while retaining other valuable attributes of the Fc region (e.g., prolonged half-life and heterodimerization). Aglycosylated antibodies can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells). Another approach is to employ Fc regions from an IgG subclass that have reduced effector function, for example, IgG2 and IgG4 antibodies are characterized by having lower levels of Fc effector functions than IgG1 and IgG3. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system (Vidarsson G. et al. Front Immunol. 5:520, 2014). Accordingly, antibodies with reduced or without Fc effector functions can be prepared by generating, e.g., a chimeric Fc region which comprises a CH2 domain from an IgG antibody of the IgG4 isotype and a CH3 domain from an IgG antibody of the IgG1 isotype, or a chimeric Fc region which comprises hinge region from IgG2 and CH2 region from IgG4 (see, e.g., Lau C. et al. J. Immunol. 191:4769-4777 (2013)), or a Fc region with mutations that result in altered Fc effector functions, e.g., reduced or no Fc functions. Such Fc regions with mutations are known in the art (see, e.g., Korean Pat. Pub. No. 10-2018-0113904).

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al., J. Immunol. 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 J Immunol 161:4083). The sequences of wild-type IgG1, IgG2, IgG3 and IgG4 hinges are known in the art (see, e.g., Kabat E A et al., (1991) Sequences of Proteins of Immunological Interest, 5th Edition, U.S. Department of Health and Human Services, NIH Publication No. 91-3242; Vidarsson G. et al. Front Immunol. 5:520 (published online Oct. 20, 2014).

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains, as well as naturally existing variants thereof (e.g., allotypes). CH1 domain sequences of IgG1, IgG2, IgG3, and IgG4 (including wildtype and allotypes) are known in the art (see, e.g., Kabat E A et al., (1991) supra and Vidarsson G. et al. Front Immunol. 5:520 (published online Oct. 20, 2014).

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as naturally existing variants thereof (e.g., allotypes). CH2 domain sequences of IgG1, IgG2, IgG3, and IgG4 (including wildtype and allotypes) are known in the art (see, e.g., Kabat E A et al., (1991) supra and Vidarsson G. et al. Front Immunol. 5:520 (published online Oct. 20, 2014). Exemplary CH2 domains include CH2 domains with mutations that modify a biological activity of an antibody, e.g., half-life and/or reduced Fc effector function (see U.S. Pub. No. 20120100140).

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as naturally existing variants thereof (e.g., allotypes). CH3 domain sequences of IgG1, IgG2, IgG3, and IgG4 (including wildtype and allotypes) are known in the art (see, e.g., Kabat E A et al., (1991) supra and Vidarsson G. et al. Front Immunol. 5:520 (published online Oct. 20, 2014). Exemplary CH3 domains include CH3 domains with mutations that modify a biological activity of an antibody, e.g., half-life (see, U.S. Pub. No. 20120100140).

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally-occurring variants within a specific isotype group, which variants differ in a few amino acids (see, e.g., Jefferis et al. (2009) mAbs 1:1). Antibodies described herein can be of any allotype. Allotypes of IgG1, IgG2, IgG3, and IgG4 are known in the art (see, e.g., Kabat E A et al., (1991) supra; Vidarsson G. et al. Front Immunol. 5:520 (published online Oct. 20, 2014); and Lefranc M P, mAbs 1:4, 1-7(2009)).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to $ET_A$ is substantially free of antibodies that specifically bind antigens other than $ET_A$). An isolated antibody that specifically binds to an epitope of $ET_A$ can, however, have cross-reactivity to other $ET_A$ proteins from different species.

As used herein, the terms "specifically binds," "specifically recognizes," "specific binding," "selective binding," and "selectively binds," are analogous terms in the context of antibodies and refer to molecules (e.g., antibodies) that bind to an antigen (e.g., epitope or immune complex) as such binding is understood by one skilled in the art.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $10^{-9}$ M or less, and most preferably between $10^{-8}$ M and $10^{-10}$ M or less, when determined by immunoassays using the predetermined antigen, but does not bind with high affinity to unrelated antigens.

According to a preferred embodiment of the present invention, the monoclonal antibody or fragment thereof includes heavy and light chain variable regions wherein the heavy chain variable region includes a CDR1 of SEQ ID NO: 38 and a CDR2 of SEQ ID NO: 39 and the light chain variable region includes a CDR1 of SEQ ID NO: 40, a CDR2 of SEQ ID NO: 41, and a CDR3 of SEQ ID NO: 42.

According to a preferred embodiment of the present invention, the CDR3 of the heavy chain variable region of the monoclonal antibody or fragment thereof includes the amino acid sequence of SEQ ID NO: 43.

According to a preferred embodiment of the present invention, the CDR3 of the heavy chain variable region of the monoclonal antibody or fragment thereof includes mutations at one or more positions selected from the group consisting of amino acid positions 4, 7, 9, 10, 11, 12, 13, and 14 in the sequence of SEQ ID NO: 43.

According to a preferred embodiment of the present invention, the CDR3 of the heavy chain variable region includes one or more mutations wherein the mutations include a substitution of the amino acid at position 4 in the sequence of SEQ ID NO: 43 to proline (P), a substitution of the amino acid at position 7 in the sequence of SEQ ID NO: 43 to leucine (L), a substitution of the amino acid at position 9 in the sequence of SEQ ID NO: 43 to valine (V), a substitution of the amino acid at position 10 in the sequence of SEQ ID NO: 43 to isoleucine (I) or histidine (H), a substitution of the amino acid at position 11 in the sequence of SEQ ID NO: 43 to phenylalanine (F) or glutamine (Q), a substitution of the amino acid at position 12 in the sequence of SEQ ID NO: 43 to glutamate (E), a substitution of the amino acid at position 13 in the sequence of SEQ ID NO: 43 to asparagine (N) or cysteine (C) or a substitution of the amino acid at position 14 in the sequence of SEQ ID NO: 43 to leucine (L).

According to a preferred embodiment of the present invention, the CDR3 of the heavy chain variable region includes the amino acid sequence selected from the group consisting of the amino acid sequences of SEQ ID NOs: 44-54.

According to a preferred embodiment of the present invention, the light chain variable region includes the amino acid sequence of SEQ ID NO: 55.

According to a preferred embodiment of the present invention, the heavy chain variable region includes the amino acid sequence selected from the group consisting of the amino acid sequences of SEQ ID NOs: 56-67.

A further aspect of the present invention provides a nucleic acid molecule encoding the monoclonal antibody or fragment thereof, a vector including the nucleic acid molecule or a host cell including the vector.

The nucleic acid molecule of the present invention may be an isolated or recombinant nucleic acid molecule. Examples of such nucleic acid molecules include single- and double-stranded DNA and RNA and their corresponding complementary sequences. The isolated nucleic acid may be isolated from a naturally occurring source. In this case, the isolated nucleic acid is separated from the peripheral gene sequence present in the genome of a subject from which the nucleic acid is to be isolated. The isolated nucleic acid may be a nucleic acid, for example, a PCR product, a cDNA molecule or an oligonucleotide, that is enzymatically or chemically synthesized from a template. In this case, the nucleic acid produced from this procedure can be understood as the isolated nucleic acid molecule. The isolated nucleic acid molecule represents a nucleic acid molecule in the form of a separate fragment or as a component of a larger nucleic acid construct. A nucleic acid is "operably linked" when arranged in a functional relationship with another nucleic acid sequence. For example, the DNA of a presequence or secretory leader is operably linked to the DNA of the polypeptide when expressed as a preprotein, which is a presecretory polypeptide. A promoter or an enhancer affecting the transcription of the polypeptide sequence is operably linked to a coding sequence or a ribosome-binding site is operably linked to a coding sequence when it is arranged such that translation is promoted. Generally, the term "operably linked" means that DNA sequences to be linked are located adjacent to each other. In the case of secretory leaders, the term "operably linked" means that the secretory leaders are present adjacent to each other in the same leading frame. However, an enhancer needs not be contiguous. The linkage is performed by ligation at a convenient restriction enzyme site. In the case where this site does not exist, a synthetic oligonucleotide adaptor or a linker is used according to a suitable method known in the art.

As used herein, the term "vector" is used to refer to a carrier into which a nucleic acid sequence can be inserted for introduction into a cell where it can be replicated. A nucleic acid sequence may be "exogenous," or "heterologous". Examples of such vectors include, but are not limited to, plasmids, cosmids, and viruses (e.g., bacteriophage). One of skill in the art may construct a vector through standard recombinant techniques (Maniatis et al., *Molecular Cloning, A Laboratory Manual*, Cold Spring Harbor Press, Cold Spring Harbor, N.Y., 1988; and Ausubel et al., In: *Current Protocols in Molecular Biology*, John, Wiley & Sons, Inc, NY, 1994, etc.).

As used herein, the term "expression vector" refers to a vector containing a nucleic acid sequence coding for at least part of a gene product capable of being transcribed. In some cases, RNA molecules are then translated into a protein, polypeptide, or peptide. Expression vectors can contain a variety of regulatory sequences. In addition to regulatory sequences that govern transcription and translation, vectors and expression vectors may contain nucleic acid sequences that serve other functions as well.

As used herein, the term "host cell" refers to any transgenic organism that is capable of replicating the vector or expressing the gene encoded by the vector. Suitable organisms include eukaryotes and prokaryotes. The host cell may be transfected or transformed by the vector. The transfection or transformation refers to a process for transferring or introducing the exogenous nucleic acid molecule into the host cell.

The host cell of the present invention is preferably a bacterial cell, CHO cell, HeLa cell, HEK293 cell, BHK-21 cell, COS7 cell, COP5 cell, A549 cell or NIH3T3 cell, but is not limited thereto.

Another aspect of the present invention provides a composition including the antibody or fragment thereof, the nucleic acid molecule or the vector.

According to a preferred embodiment of the present invention, the composition is a pharmaceutical composition for preventing or treating hypertension or cancer.

The pharmaceutical composition of the present invention may include (a) the monoclonal antibody or fragment thereof, the nucleic acid molecule or the vector including the nucleic acid molecule (b) a pharmaceutically acceptable carrier.

Another aspect of the present invention provides a method for treating cancer or hypertension including administering to a subject a pharmaceutically effective amount of the monoclonal antibody or fragment thereof, the nucleic acid molecule or the vector.

Another aspect of the present invention provides use of the monoclonal antibody or fragment thereof, the nucleic acid molecule or the vector in the preparation of a pharmaceutical composition for treating cancer or hypertension.

As used herein, "administering" refers to the physical introduction of a therapeutic agent or a composition comprising a therapeutic agent to a subject, using any of the various methods and delivery systems known to those skilled in the art. The different routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

The type of the cancer to be prevented or treated by the pharmaceutical composition of the present invention is not limited. The pharmaceutical composition of the present invention can be administered to treat a variety of cancers, including: leukemias; lymphomas such as acute lymphocytic leukemia, acute nonlymphocytic leukemias, chronic lymphocytic leukemia, chronic myelogenous leukemia, Hodgkin's disease, non-Hodgkin's lymphomas, and multiple myeloma; childhood solid tumors such as brain tumors, glioblastoma, neuroblastoma, rhabdomyosarcoma, retinoblastoma, Wilms tumor, bone tumors, and soft-tissue sarcomas; and common solid tumors of adults such as lung cancer, breast cancer, prostate cancer, urinary cancers, uterine cancers, oral cancers, pancreatic cancer, melanoma and other skin cancers, stomach cancer, colon cancer, ovarian cancer, brain tumors, liver cancer, laryngeal cancer, thyroid cancer, esophageal cancer, and testicular cancer.

The subject administered the monoclonal antibody or fragment thereof, the nucleic acid molecule, the vector including the nucleic acid molecule or the pharmaceutical composition including the monoclonal antibody or fragment thereof, the nucleic acid molecule or the vector includes any human or non-human animal. The term "non-human animal" includes all vertebrates, e.g., mammals and non-mammals, such as non-human primates, sheep, dog, cow, chickens, amphibians, reptiles, etc.

The pharmaceutically acceptable carriers are those that are commonly used for formulation. Examples of the pharmaceutically acceptable carriers include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further include one or more additives selected from the group consisting of lubricating agents, wetting agents, sweetening agents, flavoring agents, emulsifying agents, suspending agents, and preservatives. Details of suitable pharmaceutically acceptable carriers and formulations can be found in *Remington's Pharmaceutical Sciences* (19th ed., 1995).

The pharmaceutical composition of the present invention can be administered orally or parenterally, preferably parenterally. Examples of suitable parenteral routes of administration include intravenous injection, local injection, and intraperitoneal injection.

A suitable dosage of the pharmaceutical composition according to the present invention may vary depending on factors such as formulation, mode of administration, patient's age, weight, sex, pathological condition, and diet, time of administration, route of administration, excretion rate, and responsiveness. A skilled physician can easily determine and prescribe a dose of the pharmaceutical composition according to the present invention effective for desired treatment and prevention. According to a preferred embodiment of the present invention, the pharmaceutical composition is administered in a daily dose of 0.0001 to 100 mg/kg.

The pharmaceutical composition of the present invention can be formulated with one or more pharmaceutically acceptable carriers and/or excipients in accordance with methods that can be easily carried out by those skilled in the art. The pharmaceutical composition can be provided in unit dosage forms or dispensed in multi-dose containers. The formulation may be in the form of a solution, suspension or emulsion in an oil or aqueous medium or may be in the form of an extract, powder, granule, tablet or capsule. The formulation may further include a dispersant or a stabilizer.

The pharmaceutical composition of the present invention may be used alone or in combination with one or more other conventional chemotherapies or radiotherapies. This combination therapy is more effective in treating cancer. One or more chemotherapeutic agents can be used in combination with the composition of the present invention. Examples of the chemotherapeutic agents include cisplatin, carboplatin, procarbazine, mechlorethamine, cyclophosphamide, ifosfamide, melphalan, chlorambucil, busulfan, nitrosourea, dactinomycin, daunorubicin, doxorubicin, bleomycin, plicamycin, mitomycin, etoposide, tamoxifen, taxol, transplatinum, 5-fluorouracil, vincristine, vinblastine, and methotrexate. The radiotherapies used in combination with the composition of the present invention may be, for example, X-ray irradiation and γ-ray irradiation.

Another aspect of the present invention provides a method for quantifying endothelin receptor type A in a sample, including treating the sample with the monoclonal antibody or fragment thereof.

The antibody or fragment thereof of the present invention can be used to accurately measure the amount of endothelin receptor type A in a sample due to its ability to specifically bind to the endothelin receptor type A.

Another aspect of the present invention provides a method for providing information necessary for the diagnosis of a disease caused by overexpression of endothelin receptor type A, including (a) separating a sample from a subject, (b) treating the sample with the monoclonal antibody or fragment thereof, and (c) determining whether the expression level of endothelin receptor type A in the sample from the subject is higher than that of endothelin receptor type A in a normal sample.

Endothelin receptor type A binds to its ligand ET-1 to cause vasoconstriction (Nature reviews drug discovery, 2011, Vol. 10, 47). In addition, endothelin receptor type A is overexpressed in a variety of cancers such as bladder cancer, lung cancer, ovarian cancer, kidney cancer, colorectal cancer, prostate cancer, breast cancer, uterine cancer, rhabdomyosarcoma, and glioblastoma and is directly involved in main cancer processes such as proliferation, migration, invasion, metastasis, and angiogenesis of cancer cells (Nature review cancer, 2013, Vol. 13, 637). For these reasons, a comparison of the expression level of endothelin receptor type A in the sample with that in a sample from a normal human can provide information necessary for the diagnosis of a disease caused by overexpression of endothelin receptor type A.

According to a preferred embodiment of the present invention, the disease caused by overexpression of endothelin receptor type A is cancer or hypertension.

Yet another aspect of the present invention provides a kit for quantifying endothelin receptor type A including the monoclonal antibody or fragment thereof.

The quantification kit of the present invention can quantify the amount of endothelin receptor type A by analyzing an antigen to the antibody through an antigen-antibody binding reaction. The antigen-antibody binding reaction is preferably selected from the group consisting of, but not limited to, enzyme-linked immunosorbent assay (ELISA), radioimmunoassay (RIA), sandwich assay, Western blotting on polyacrylamide gel, immunoblotting assay, and immunohistochemical staining.

A support for the antigen-antibody binding reaction is selected from the group consisting of, but not limited to, nitrocellulose membranes, PVDF membranes, well plates made of polyvinyl or polystyrene resin, and slide glasses.

The secondary antibody is preferably labeled with a reagent that develops a color. The color-developing reagent can be selected from the group consisting of fluoresceins and dyes. The fluoresceins may be, for example, horseradish peroxidase (HRP), alkaline phosphatase, colloid gold, poly-L-lysine-fluorescein isothiocyanate (FITC), and rhodamine-B-isothiocyanate (RITC). A substrate for inducing color development is preferably used depending on the color-developing reagent. The substrate is preferably selected from the group consisting of, but not limited to, 3,3',5,5'-tetramethylbenzidine (TMB), 2,2'-azino-bis(3-ethylbenzothiazoline)-6-sulfonic acid (ABTS), and ophenylenediamine (OPD).

Effects of the Invention

The features and advantages of the present invention are summarized as follows.
(i) The monoclonal antibody or fragment thereof of present invention recognizes and specifically binds to the extracellular domain of endothelin receptor type A as an antigen.
(ii) The pharmaceutical composition of the present invention, which includes the monoclonal antibody or fragment thereof, the nucleic acid molecule or the vector, is effective in preventing or treating cancer or hypertension.
(iii) Due to its function of inhibiting the signal transduction pathways of endothelin receptor type A, the monoclonal antibody of the present invention is suitable for use in a therapeutic agent for hypertension or cancer in which endothelin receptor type A is involved.

MODE FOR CARRYING OUT THE INVENTION

Figure 1:
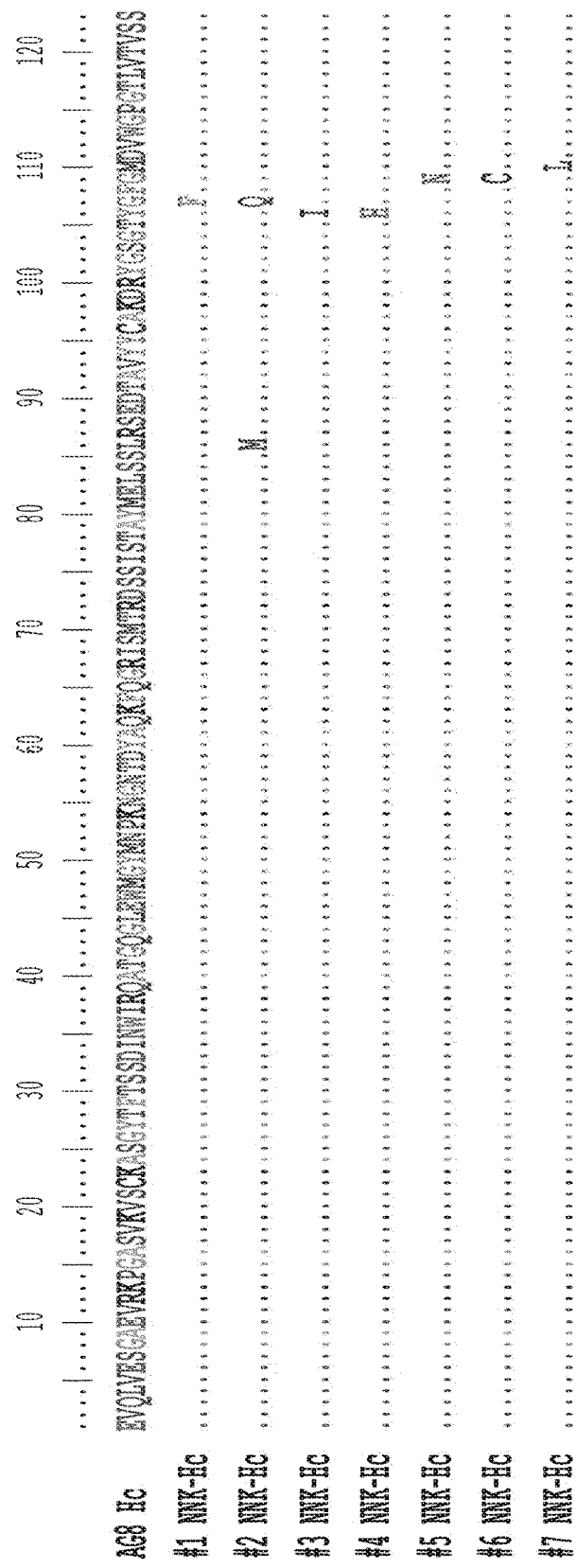
FIG. 1 (SEQ ID NOs: 73 and 14-20) shows a constructed affinity maturation bacteriophage antibody library.

The present invention will be more specifically explained with reference to the following examples. It will be evident to those skilled in the art that the scope of the present invention is not limited by these examples according to the gist of the present invention.

Examples

<Example 1> Construction of Bacteriophage Antibody Library Using Clone Sequences of $ET_A$-Specific Binding Antibody (AG8)

Based on the sequence of a developed $ET_A$-specific binding antibody (AG8, Korean Patent No. 10-2014383), a library was constructed to develop antibodies with improved binding to an existing target antigen and improved efficacy. Specifically, an affinity maturation library was constructed using degenerate NNK codons such that 13 amino acid sequences of the heavy chain CDR3 of the antibody were randomly replaced with a total of 20 amino acids. CDR3 is a complementarity-determining region (CDR) known to play an important role in antigen-antibody binding. For DNA primer design for antibody library construction and DNA gene sequence amplification by PCR, and library construction, refer to Manfred T Reetz & José Daniel Carballeira, Iterative saturation mutagenesis (ISM) for rapid directed evolution of functional enzymes, Nature Protocols, 2(4), 891-903 and Frances H. Arnold & George Georgiou, Directed Evolution Library Creation: Methods and Protocols, Humana press, 2010. More specifically, primers were constructed such that the sequences of the framework and CDR1 and CDR2 regions of the heavy chain of the antibody AG8 described in the previous Korean patent and the sequences of the framework and CDR1, CDR2, and CDR3 regions of the light chain of the antibody AG8 were conserved and only the CDR3 sequence of the heavy chain was randomly replaced with ~20 amino acids. A plasmid DNA of affinity maturation antibody libraries was prepared by using gene amplification and cloning techniques. Thereafter, antibodies capable of selective binding to $ET_A$ were screened using the phage display technique. To this end, the plasmid DNA of affinity maturation antibody libraries was transformed into *E. coli* (ER2738) to construct an affinity maturation bacteriophage antibody library. The gene sequences of randomly selected clones from the constructed antibody library are shown in FIG. 1.

TABLE 1

| SEQ ID NO | Name | Sequence |
|---|---|---|
| 1 | AG8-CDR3H-NNK1-RV | GGGTTCCCGGGCCCCA GACGTCCATACCGAAGCCATAAGTCCCCGAACCATAM NNATCTTTTGC ACAGTAATACACGGCCGTGTCCTC |
| 2 | AG8-CDR3H-NNK2-RV | GGGTTCCCGGGCCCCA GACGTCCATACCGAAGCCATAAGTCCCCGAACCMNNC CTATCTTTTGC ACAGTAATACACGGCCGTGTCCTC |
| 3 | AG8-CDR3H-NNK3-RV | GGGTTCCCGGGCCCCA GACGTCCATACCGAAGCCATAAGTCCCCGAMNNATAC CTATCTTTTGC ACAGTAATACACGGCCGTGTCCTC |
| 4 | AG8-CDR3H-NNK4-RV | GGGTTCCCGGGCCCCA GACGTCCATACCGAAGCCATAAGTCCCMNNACCATAC CTATCTTTTGC ACAGTAATACACGGCCGTGTCCTC |
| 5 | AG8-CDR3H-NNK5-RV | GGGTTCCCGGGCCCCA GACGTCCATACCGAAGCCATAAGTMNNCGAACCATAC CTATCTTTTGC ACAGTAATACACGGCCGTGTCCTC |
| 6 | AG8-CDR3H-NNK6-RV | GGGTTCCCGGGCCCCA GACGTCCATACCGAAGCCATAMNNCCCCGAACCATAC CTATCTTTTGC ACAGTAATACACGGCCGTGTCCTC |
| 7 | AG8-CDR3H-NNK7-RV | GGGTTCCCGGGCCCCA GACGTCCATACCGAAGCCMNNAGTCCCCGAACCATAC CTATCTTTTGC ACAGTAATACACGGCCGTGTCCTC |
| 8 | AG8-CDR3H-NNK8-RV | GGGTTCCCGGGCCCCA GACGTCCATACCGAAMNNATAAGTCCCCGAACCATAC CTATCTTTTGC ACAGTAATACACGGCCGTGTCCTC |
| 9 | AG8-CDR3H-NNK9-RV | GGGTTCCCGGGCCCCA GACGTCCATACCMNNGCCATAAGTCCCCGAACCATAC CTATCTTTTGC ACAGTAATACACGGCCGTGTCCTC |
| 10 | AG8-CDR3HR-NNK10-RV | GGGTTCCCGGGCCCCA GACGTCCATMNNGAAGCCATAAGTCCCCGAACCATAC CTATCTTTTGC ACAGTAATACACGGCCGTGTCCTC |

TABLE 1-continued

| SEQ ID NO | Name | Sequence |
|---|---|---|
| 11 | AG8-CDR3H-NNK11-RV | GGGTTCCCGGGCCCCA GACGTCMNNACCGAAGCCATAAGTCCCCGAACCATAC CTATCTTTTGC ACAGTAATACACGGCCGTGTCCTC |
| 12 | AG8-CDR3HR-NNK12-RV | GGGTTCCCGGGCCCCA GACMNNCATACCGAAGCCATAAGTCCCCGAACCATAC CTATCTTTTGC ACAGTAATACACGGCCGTGTCCTC |
| 13 | AG8-CDR3HR-NNK13-RV | GGGTTCCCGGGCCCCA MNNGTCCATACCGAAGCCATAAGTCCCCGAACCATAC CTATCTTTTGC ACAGTAATACACGGCCGTGTCCTC |

Sequences of the degenerate NNK primers used for library construction (5'→3')

TABLE 2

| SEQ ID NO | Name | Sequence |
|---|---|---|
| 14 | #1NNK | EVQLVESGAEVRKPGASVKVSCKASGYTFTSSDINWIRQ ATGQGLEWMGYMNPKNGNTDYAQKFQGRISMTRDSSIS TAYMELSSLRSEDTAVYYCAKDRYGSGTYFFGMDVWGP GTLVTVSS |
| 15 | #2NNK | EVQLVESGAEVRKPGASVKVSCKASGYTFTSSDINWIRQ ATGQGLEWMGYMNPKNGNTDYAQKFQGRISMTRDSSIS TAYMELSSMRSEDTAVYYCAKDRYGSGTYQFGMDVWG PGTLVTVSS |
| 16 | #3NNK | EVQLVESGAEVRKPGASVKVSCKASGYTFTSSDINWIRQ ATGQGLEWMGYMNPKNGNTDYAQKFQGRISMTRDSSIS TAYMELSSLRSEDTAVYYCAKDRYGSGTIGFGMDWGP GTLVTVSS |
| 17 | #4NNK | EVQLVESGAEVRKPGASVKVSCKASGYTFTSSDINWIRQ ATGQGLEWMGYMNPKNGNTDYAQKFQGRISMTRDSSIS TAYMELSSLRSEDTAVYYCAKDRYGSGTHGFGMDVWG PGTLVTVSS |
| 18 | #5NNK | EVQLVESGAEVRKPGASVKVSCKASGYTFTSSDINWIRQ ATGQGLEWMGYMNPKNGNTDYAQKFQGRISMTRDSSIS TAYMELSSLRSEDTAVYYCAKDRYGSGTYGFNMDVWG PGTLVTVSS |
| 19 | #6NNK | EVQLVESGAEVRKPGASVKVSCKASGYTFTSSDINWIRQ ATGQGLEWMGYMNPKNGNTDYAQKFQGRISMTRDSSIS TAYMELSSLRSEDTAVYYCAKDRYGSGTYGFCMDVWG PGTLVTVSS |
| 20 | #7NNK | EVQLVESGAEVRKPGASVKVSCKASGYTFTSSDINWIRQ ATGQGLEWMGYMNPKNGNTDYAQKFQGRISMTRDSSIS TAYMELSSLRSEDTAVYYCAKDRYGSGTYGFGLDVWGP GTLVTVSS |

Randomly selected sequences (amino acid sequences) from the constructed library

TABLE 3

| SEQ ID NO | Name | Sequence |
|---|---|---|
| 21 | #1NNK | GAGGTGCAGCTGGTGGAGTCTGGGGCTGAGGTGAGGAAGCCTGGGG CCTCAGTGAAGGTCTCCTGCAAGGCTTCTGGATACACCTTCACCAGT TCTGATATCAACTGGATTCGACAGGCCACTGGACAAGGGCTTGAGTG GATGGGATACATGAACCCTAAAAATGGAAACACAGACTATGCACAG AAGTTCCAGGGCAGAATCTCCATGACCAGGGACAGCTCCATAAGCA CAGCCTACATGGAGCTGAGCAGCCTGAGATCTGAGGACACGGCCGT GTATTACTGTGCAAAAGATAGGTATGGTTCGGGGACTTATTTTTTCG GTATGGACGTCTGGGGCCCGGGAACCCTGGTCACCGTCTCCTCA |
| 22 | #2NNK | GAGGTGCAGCTGGTGGAGTCTGGGGCTGAGGTGAGGAAGCCTGGGG CCTCAGTGAAGGTCTCCTGCAAGGCTTCTGGATACACCTTCACCAGT TCTGATATCAACTGGATTCGACAGGCCACTGGACAAGGGCTTGAGTG GATGGGATACATGAACCCTAAAAATGGAAACACAGACTATGCACAG AAGTTCCAGGGCAGAATCTCCATGACCAGGGACAGCTCCATAAGCA CAGCCTACATGGAGCTGAGCAGCCTGAGATCTGAGGACACGGCCGT GTATTACTGTGCAAAAGATAGGTATGGTTCGGGGACTTATCAGTTCG GTATGGACGTCTGGGGCCCGGGAACCCTGGTCACCGTCTCCTCA |
| 23 | #3NNK | GAGGTGCAGCTGGTGGAGTCTGGGGCTGAGGTGAGGAAGCCTGGGG CCTCAGTGAAGGTCTCCTGCAAGGCTTCTGGATACACCTTCACCAGT TCTGATATCAACTGGATTCGACAGGCCACTGGACAAGGGCTTGAGTG GATGGGATACATGAACCCTAAAAATGGAAACACAGACTATGCACAG AAGTTCCAGGGCAGAATCTCCATGACCAGGGACAGCTCCATAAGCA CAGCCTACATGGAGCTGAGCAGCCTGAGATCTGAGGACACGGCCGT GTATTACTGTGCAAAAGATAGGTATGGTTCGGGGACTATTGGCTTCG GTATGGACGTCTGGGGCCCGGGAACCCTGGTCACCGTCTCCTCA |
| 24 | #4NNK | GAGGTGCAGCTGGTGGAGTCTGGGGCTGAGGTGAGGAAGCCTGGGG CCTCAGTGAAGGTCTCCTGCAAGGCTTCTGGATACACCTTCACCAGT TCTGATATCAACTGGATTCGACAGGCCACTGGACAAGGGCTTGAGTG |

TABLE 3-continued

| SEQ ID NO | Name | Sequence |
|---|---|---|
| | | GATGGGATACATGAACCCTAAAAATGGAAACACAGACTATGCACAG<br>AAGTTCCAGGGCAGAATCTCCATGACCAGGGACAGCTCCATAAGCA<br>CAGCCTACATGGAGCTGAGCAGCCTGAGATCTGAGGACACGGCCGT<br>GTATTACTGTGCAAAAGATAGGTATGGTTCGGGGACTCATGGCTTCG<br>GTATGGACGTCTGGGGCCCGGGAACCCTGGTCACCGTCTCCTCA |
| 25 | #5NNK | GAGGTGCAGCTGGTGGAGTCTGGGGCTGAGGTGAGGAAGCCTGGGG<br>CCTCAGTGAAGGTCTCCTGCAAGGCTTCTGGATACACCTTCACCAGT<br>TCTGATATCAACTGGATTCGACAGGCCACTGGACAAGGGCTTGAGTG<br>GATGGGATACATGAACCCTAAAAATGGAAACACAGACTATGCACAG<br>AAGTTCCAGGGCAGAATCTCCATGACCAGGGACAGCTCCATAAGCA<br>CAGCCTACATGGAGCTGAGCAGCCTGAGATCTGAGGACACGGCCGT<br>GTATTACTGTGCAAAAGATAGGTATGGTTCGGGGACTTATGGCTTCA<br>ATATGGACGTCTGGGGCCCGGGAACCCTGGTCACCGTCTCCTCA |
| 26 | #6NNK | GAGGTGCAGCTGGTGGAGTCTGGGGCTGAGGTGAGGAAGCCTGGGG<br>CCTCAGTGAAGGTCTCCTGCAAGGCTTCTGGATACACCTTCACCAGT<br>TCTGATATCAACTGGATTCGACAGGCCACTGGACAAGGGCTTGAGTG<br>GATGGGATACATGAACCCTAAAAATGGAAACACAGACTATGCACAG<br>AAGTTCCAGGGCAGAATCTCCATGACCAGGGACAGCTCCATAAGCA<br>CAGCCTACATGGAGCTGAGCAGCCTGAGATCTGAGGACACGGCCGT<br>GTATTACTGTGCAAAAGATAGGTATGGTTCGGGGACTTATGGCTTCT<br>GTATGGACGTCTGGGGCCCGGGAACCCTGGTCACCGTCTCCTCA |
| 27 | #7NNK | GAGGTGCAGCTGGTGGAGTCTGGGGCTGAGGTGAGGAAGCCTGGGG<br>CCTCAGTGAAGGTCTCCTGCAAGGCTTCTGGATACACCTTCACCAGT<br>TCTGATATCAACTGGATTCGACAGGCCACTGGACAAGGGCTTGAGTG<br>GATGGGATACATGAACCCTAAAAATGGAAACACAGACTATGCACAG<br>AAGTTCCAGGGCAGAATCTCCATGACCAGGGACAGCTCCATAAGCA<br>CAGCCTACATGGAGCTGAGCAGCCTGAGATCTGAGGACACGGCCGT<br>GTATTACTGTGCAAAAGATAGGTATGGTTCGGGGACTTATGGCTTCG<br>GTCTGGACGTCTGGGGCCCGGGAACCCTGGTCACCGTCTCCTCA |

Randomly selected sequences (nucleotide sequences) from the constructed library

Figure 2:
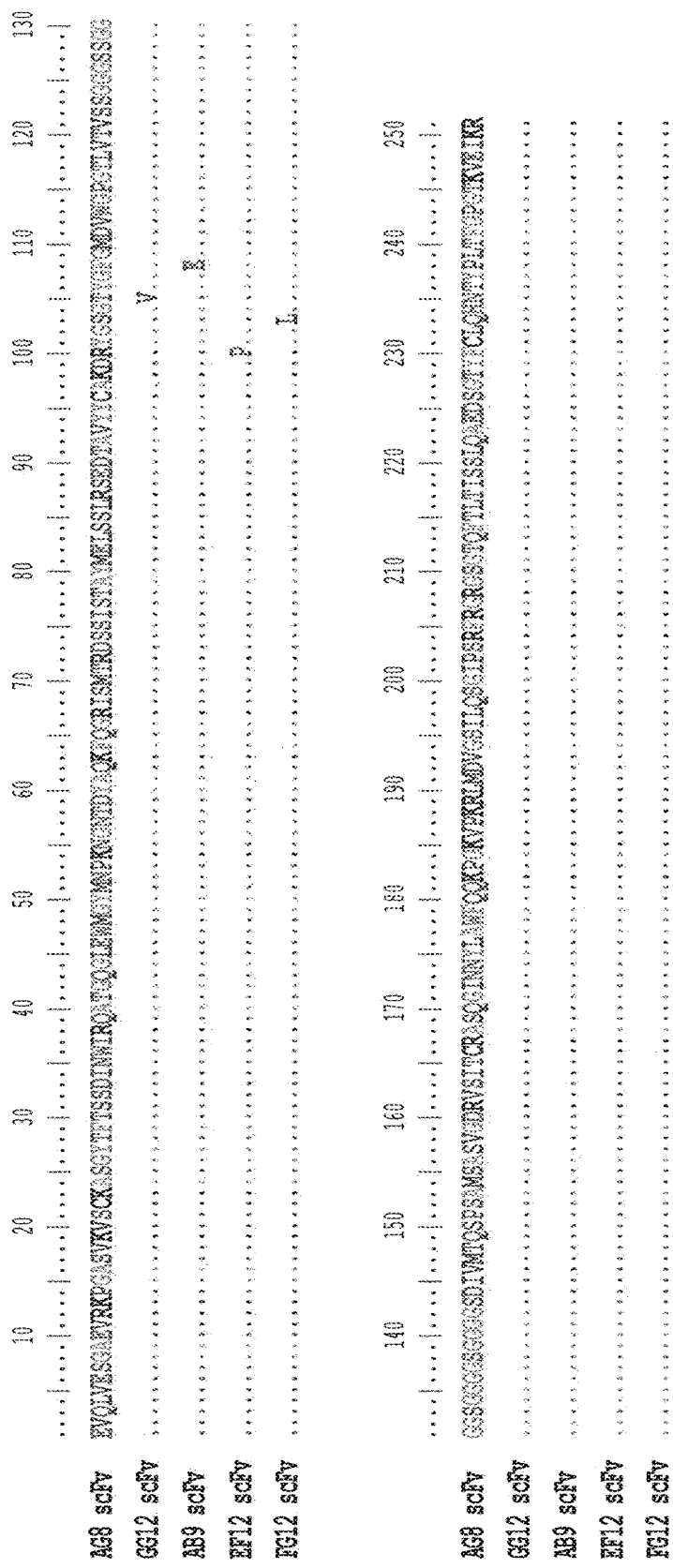
FIG. 2 (SEQ ID NOs: 28-32) shows the sequences of developed antibodies selectively binding to $ET_A$.
Figure 3:
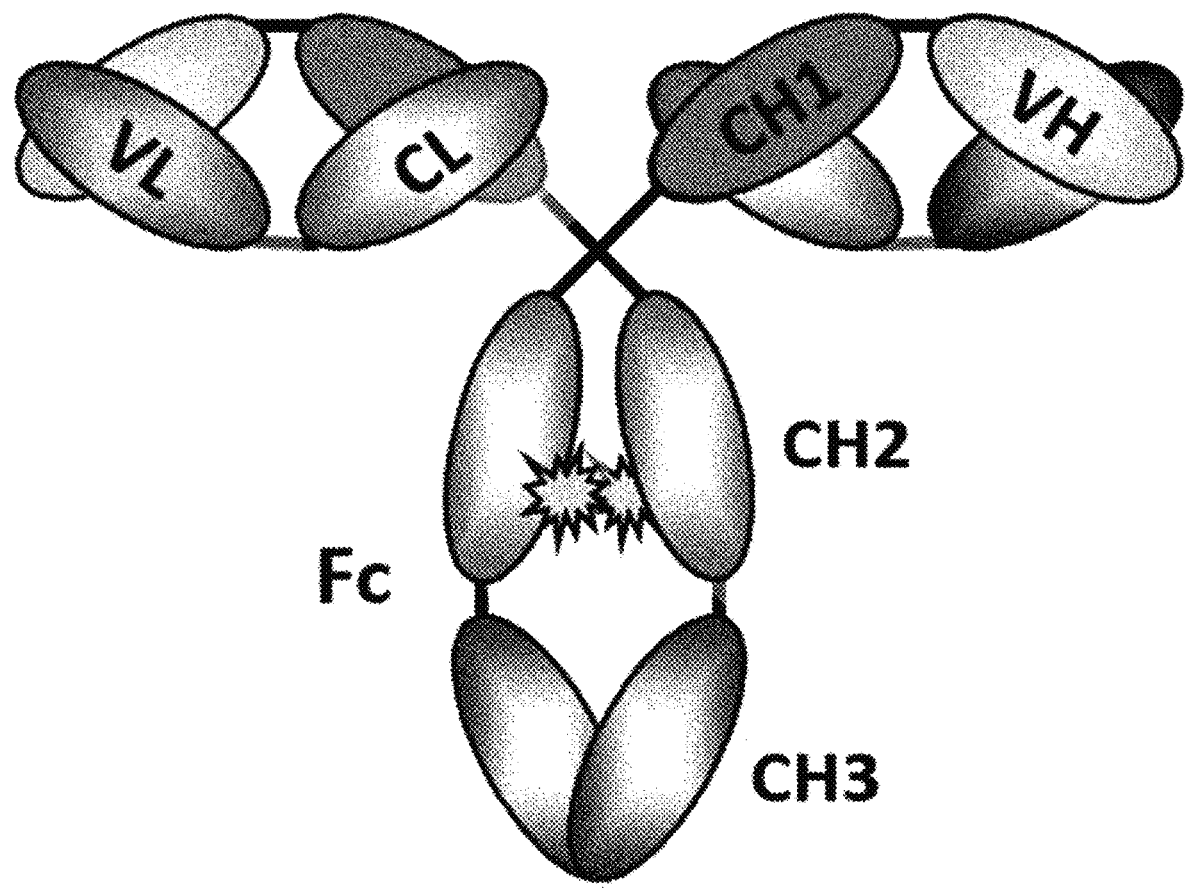
FIG. 3 shows the structure of an expressed IgG.
Figure 4:
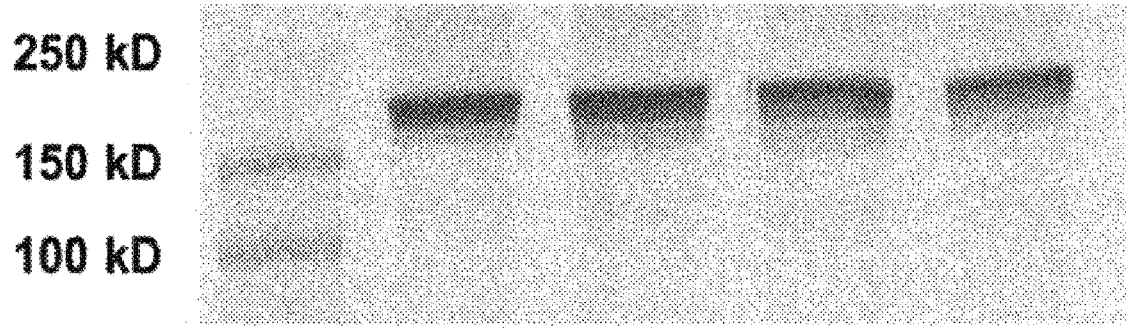
FIG. 4 shows the results obtained after purification of developed antibodies expressed in animal cells.

<Example 2> Conversion of the Developed ET$_A$-Specific Antibodies to Full-Length IgGs and Expression and Purification in Animal Cells Phages were created using the VCSM13 helper phage based on the constructed antibody library. Thereafter, biopanning was performed using magnetic beads to discover antibodies selective for the outer cell membrane and the discovered antibodies were sequenced. The results are shown in FIG. 2. The discovered antibodies were converted to immunoglobulins (IgGs) for expression, purification, and stabilization in animal cells. To this end, expression vectors were prepared, and the antibodies were expressed and purified in animal cells (see, Mazor, Y., Barnea, I., Keydar, I., & Benhar, I. (2007) Antibody internalization studied using a novel IgG binding toxin fusion. Journal of Immunological Methods, 321(1-2), 41-59). An exemplary structure of each antibody is shown in FIG. 3. The results of SDS-PAGE for the proteins expressed in animal cells and obtained in high purity by affinity chromatography are shown in FIG. 4.

TABLE 4

| SEQ ID NO | Name | Sequence |
|---|---|---|
| 28 | AG8 | EVQLVESGAEVRKPGASVKVSCKASGYTFTSSDINWIRQATGQGL<br>EWMGYMNPKNGNTDYAQKFQGRISMTRDSSISTAYMELSSLRSE<br>DTAVYYCAKDRYGSGTYGFGMDVWGPGTLVTVSSGGGSSGGGG<br>SGGGGSGGGGSDIVMTQSPSAMSASVGDRVSITCRASQGINNYLA<br>WFQQKPGKVPKRLMDVGSILQSGIPSRFRGRGSGTQFTLTISSLQA<br>EDSGTYFCLQHNTYPLTFGPGTKVEIKR |
| 29 | EF12 | EVQLVESGAEVRKPGASVKVSCKASGYTFTSSDINWIRQATGQGL<br>EWMGYMNPKNGNTDYAQKFQGRISMTRDSSISTAYMELSSLRSE<br>DTAVYYCAKDPYGSGTYGFGMDVWGPGTLVTVSSGGGSSGGGG<br>SGGGGSGGGGSDIVMTQSPSAMSASVGDRVSITCRASQGINNYLA<br>WFQQKPGKVPKRLMDVGSILQSGIPSRFRGRGSGTQFTLTISSLQA<br>EDSGTYFCLQHNTYPLTFGPGTKVEIKR |
| 30 | GG12 | EVQLVESGAEVRKPGASVKVSCKASGYTFTSSDINWIRQATGQGL<br>EWMGYMNPKNGNTDYAQKFQGRISMTRDSSISTAYMELSSLRSE<br>DTAVYYCAKDRYGSGVYGFGMDVWGPGTLVTVSSGGGSSGGGG<br>SGGGGSGGGGSDIVMTQSPSAMSASVGDRVSITCRASQGINNYLA<br>WFQQKPGKVPKRLMDVGSILQSGIPSRFRGRGSGTQFTLTISSLQA<br>EDSGTYFCLQHNTYPLTFGPGTKVEIKR |
| 31 | FG12 | EVQLVESGAEVRKPGASVKVSCKASGYTFTSSDINWIRQATGQGL<br>EWMGYMNPKNGNTDYAQKFQGRISMTRDSSISTAYMELSSLRSE<br>DTAVYYCAKDRYGLGTYGFGMDVWGPGTLVTVSSGGGSSGGGG |

TABLE 4-continued

| SEQ ID NO | Name | Sequence |
|---|---|---|
| | | SGGGGSGGGGSDIVMTQSPSAMSASVGDRVSITCRASQGINNYLA<br>WFQQKPGKVPKRLMDVGSILQSGIPSRFRGRGSGTQFTLTISSLQA<br>EDSGTYFCLQHNTYPLTFGPGTKVEIKR |
| 32 | AB9 | EVQLVESGAEVRKPGASVKVSCKASGYTFTSSDINWIRQATGQGL<br>EWMGYMNPKNGNTDYAQKFQGRISMTRDSSISTAYMELSSLRSE<br>DTAVYYCAKDRYGSGTYGEGMDVWGPGTLVTVSSGGGSSGGGG<br>SGGGGSGGGGSDIVMTQSPSAMSASVGDRVSITCRASQGINNYLA<br>WFQQKPGKVPKRLMDVGSILQSGIPSRFRGRGSGTQFTLTISSLQA<br>EDSGTYFCLQHNTYPLTFGPGTKVEIKR | scFv sequences (amino acid sequences) of the 5 antibodies showing inhibitory activities for cell signaling induced by $ET_A$

TABLE 5

| SEQ ID NO | Name | Sequence |
|---|---|---|
| 33 | AG8 | GAGGTGCAGCTGGTGGAGTCTGGGGCTGAGGTGAGGAAGCCTGGGGCCTCAGTGAAGG<br>TCTCCTGCAAGGCTTCTGGATACACCTTCACCAGTTCTGATATCAACTGGATTCGACAGG<br>CCACTGGACAAGGGCTTGAGTGGATGGGATACATGAACCCTAAAAATGGAAACACAGA<br>CTATGCACAGAAGTTCCAGGGCAGAATCTCCATGACCAGGGACAGCTCCATAAGCACAG<br>CCTACATGGAGCTGAGCAGCCTGAGATCTGAGGACACGGCCGTGTATTACTGTGCAAAA<br>GATAGGTATGGTTCGGGGACTTATGGCTTCGGTATGGACGTCTGGGGCCCGGGAACCCT<br>GGTCACCGTCTCCTCAGGTGGAGGGAGCTCTGGAGGTGGAGGTTCCGGTGGAGGTGGAT<br>CTGGTGGAGGTGGAAGTGACATCGTGATGACCCAGTCTCCATCTGCCATGTCTGCATCTG<br>TCGGAGACAGAGTCTCCATCACTTGTCGGGCGAGTCAGGGCATTAACAATTATTTAGCC<br>TGGTTTCAGCAGAAACCAGGGAAAGTCCCTAAGCGCCTGATGGATGTTGGATCCATTTT<br>GCAAAGTGGCATCCCATCAAGATTCAGGGGCAGAGGCTCTGGGACACAATTCACTCTCA<br>CAATCAGCAGCCTGCAGGCAGAAGATTCAGGCACTTATTTCTGTCTTCAGCATAATACTT<br>ACCCCCTCACTTTCGGCCCTGGGACCAAGGTGGAGATCAAACGT |
| 34 | EF12 | GAGGTGCAGCTGGTGGAGTCTGGGGCTGAGGTGAGGAAGCCTGGGGCCTCAGTGAAGG<br>TCTCCTGCAAGGCTTCTGGATACACCTTCACCAGTTCTGATATCAACTGGATTCGACAGG<br>CCACTGGACAAGGGCTTGAGTGGATGGGATACATGAACCCTAAAAATGGAAACACAGA<br>CTATGCACAGAAGTTCCAGGGCAGAATCTCCATGACCAGGGACAGCTCCATAAGCACAG<br>CCTACATGGAGCTGAGCAGCCTGAGATCTGAGGACACGGCCGTGTATTACTGTGCAAAA<br>GATCCGTATGGTTCGGGGACTTATGGCTTCGGTATGGACGTCTGGGGCCCGGGAACCCT<br>GGTCACCGTCTCCTCAGGTGGAGGGAGCTCTGGAGGTGGAGGTTCCGGTGGAGGTGGAT<br>CTGGTGGAGGTGGAAGTGACATCGTGATGACCCAGTCTCCATCTGCCATGTCTGCATCTG<br>TCGGAGACAGAGTCTCCATCACTTGTCGGGCGAGTCAGGGCATTAACAATTATTTAGCC<br>TGGTTTCAGCAGAAACCAGGGAAAGTCCCTAAGCGCCTGATGGATGTTGGATCCATTTT<br>GCAAAGTGGCATCCCATCAAGATTCAGGGGCAGAGGCTCTGGGACACAATTCACTCTCA<br>CAATCAGCAGCCTGCAGGCAGAAGATTCAGGCACTTATTTCTGTCTTCAGCATAATACTT<br>ACCCCCTCACTTTCGGCCCTGGGACCAAGGTGGAGATCAAACGT |
| 35 | GG12 | GAGGTGCAGCTGGTGGAGTCTGGGGCTGAGGTGAGGAAGCCTGGGGCCTCAGTGAAGG<br>TCTCCTGCAAGGCTTCTGGATACACCTTCACCAGTTCTGATATCAACTGGATTCGACAGG<br>CCACTGGACAAGGGCTTGAGTGGATGGGATACATGAACCCTAAAAATGGAAACACAGA<br>CTATGCACAGAAGTTCCAGGGCAGAATCTCCATGACCAGGGACAGCTCCATAAGCACAG<br>CCTACATGGAGCTGAGCAGCCTGAGATCTGAGGACACGGCCGTGTATTACTGTGCAAAA<br>GATAGGTATGGTTCGGGGGTGTATGGCTTCGGTATGGACGTCTGGGGCCCGGGAACCCT<br>GGTCACCGTCTCCTCAGGTGGAGGGAGCTCTGGAGGTGGAGGTTCCGGTGGAGGTGGAT<br>CTGGTGGAGGTGGAAGTGACATCGTGATGACCCAGTCTCCATCTGCCATGTCTGCATCTG<br>TCGGAGACAGAGTCTCCATCACTTGTCGGGCGAGTCAGGGCATTAACAATTATTTAGCC<br>TGGTTTCAGCAGAAACCAGGGAAAGTCCCTAAGCGCCTGATGGATGTTGGATCCATTTT<br>GCAAAGTGGCATCCCATCAAGATTCAGGGGCAGAGGCTCTGGGACACAATTCACTCTCA<br>CAATCAGCAGCCTGCAGGCAGAAGATTCAGGCACTTATTTCTGTCTTCAGCATAATACTT<br>ACCCCCTCACTTTCGGCCCTGGGACCAAGGTGGAGATCAAACGT |
| 36 | FG12 | GAGGTGCAGCTGGTGGAGTCTGGGGCTGAGGTGAGGAAGCCTGGGGCCTCAGTGAAGG<br>TCTCCTGCAAGGCTTCTGGATACACCTTCACCAGTTCTGATATCAACTGGATACGACAGG<br>CCACTGGACAAGGGCTTGAGTGGATGGGATACATGAACCCTAAAAATGGAAACACAGA<br>CTATGCACAGAAGTTCCAGGGCAGAATCTCCATGACCAGGGACAGCTCCATAAGCACAG<br>CCTACATGGAGCTGAGCAGCCTGAGATCTGAGGACACGGCCGTGTATTACTGTGCAAAA<br>GATAGGTATGGTCTTGGGACTTATGGCTTCGGTATGGACGTCTGGGGCCCGGGAACCCT<br>GGTCACCGTCTCCTCAGGTGGAGGGAGCTCTGGAGGTGGAGGTTCCGGTGGAGGTGGAT<br>CTGGTGGAGGTGGAAGTGACATCGTGATGACCCAGTCTCCATCTGCCATGTCTGCATCTG<br>TCGGAGACAGAGTCTCCATCACTTGTCGGGCGAGTCAGGGCATTAACAATTATTTAGCC<br>TGGTTTCAGCAGAAACCAGGGAAAGTCCCTAAGCGCCTGATGGATGTTGGATCCATTTT<br>GCAAAGTGGCATCCCATCAAGATTCAGGGGCAGAGGCTCTGGGACACAATTCACTCTCA<br>CAATCAGCAGCCTGCAGGCAGAAGATTCAGGCACTTATTTCTGTCTTCAGCATAATACTT<br>ACCCCCTCACTTTCGGCCCTGGGACCAAGGTGGAGATCAAACGT |
| 37 | AB9 | GAGGTGCAGCTGGTGGAGTCTGGGGCTGAGGTGAGGAAGCCTGGGGCCTCAGTGAAGG<br>TCTCCTGCAAGGCTTCTGGATACACCTTCACCAGTTCTGATATCAACTGGATTCGACAGG<br>CCACTGGACAAGGGCTTGAGTGGATGGGATACATGAACCCTAAAAATGGAAACACAGA |

TABLE 5-continued

| SEQ ID NO | Name | Sequence |
|---|---|---|
| | | CTATGCACAGAAGTTCCAGGGCAGAATCTCCATGACCAGGGACAGCTCCATAAGCACAG |
| | | CCTACATGGAGCTGAGCAGCCTGAGATCTGAGGACACGGCCGTGTATTACTGTGCAAAA |
| | | GATAGGTATGGTTCGGGGACTTATGGCGAGGGTATGGACGTCTGGGGCCCGGGAACCCT |
| | | GGTCACCGTCTCCTCAGGTGGAGGGAGCTCTGGAGGTGGAGGTTCCGGTGGAGGTGGAT |
| | | CTGGTGGAGGTGGAAGTGACATCGTGATGACCCAGTCTCCATCTGCCATGTCTGCATCTG |
| | | TCGGAGACAGAGTCTCCATCACTTGTCGGGCGAGTCAGGGCATTAACAATTATTTAGCC |
| | | TGGTTTCAGCAGAAACCAGGGAAAGTCCCTAAGCGCCTGATGGATGTTGGATCCATTTT |
| | | GCAAAGTGGCATCCCATCAAGATTCAGGGGCAGAGGCTCTGGGACACAATTCACTCTCA |
| | | CAATCAGCAGCCTGCAGGCAGAAGATTCAGGCACTTATTTCTGTCTTCAGCATAATACTT |
| | | ACCCCCTCACTTTCGGCCCTGGGACCAAGGTGGAGATCAAACGT | scFv sequences (nucleotide sequences) of the 5 antibodies showing inhibitmy activities for cell signaling induced by $ET_A$

TABLE 6

| SEQ ID NO | Name | Sequence |
|---|---|---|
| 38 | HCDR1 | GYTFTSS |
| 39 | HCDR2 | MNPKNGNT |
| 40 | LCDR1 | QGINNY |
| 41 | LCDR2 | VGS |
| 42 | LCDR3 | LQHNTYPLT |

Heavy chain CDR1 and CDR2 sequences and light chain CDR1, CDR2, and CDR3 sequences of the developed antibody

TABLE 7

| SEQ ID NO | Name | Sequence |
|---|---|---|
| 43 | AG8 | AKDRYGSGTYGFGMDV |
| 44 | #1NNK | AKDRYGSGTYFFGMDV |
| 45 | #2NNK | AKDRYGSGTYQFGMDV |
| 46 | #3NNK | AKDRYGSGTIGFGMDV |
| 47 | #4NNK | AKDRYGSGTHGFGMDV |
| 48 | #5NNK | AKDRYGSGTYGFNMDV |
| 49 | #6NNK | AKDRYGSGTYGFCMDV |
| 50 | #7NNK | AKDRYGSGTYGFGLDV |
| 51 | EF12 | AKDPYGSGTYGFGMDV |
| 52 | GG12 | AKDRYGSGVYGFGMDV |
| 53 | FG12 | AKDRYGLGTYGFGMDV |
| 54 | AB9 | AKDRYGSGTYGEGMDV |

Heavy chain CDR3 (HCDR3) sequences of the developed antibodies

TABLE 8

| SEQ ID NO | Sequence |
|---|---|
| 55 | DIVMTQSPSAMSASVGDRVSITCRAS***QGINNY***LAWFQQKPGKVPKRLMD***VGS***ILQSGIPSRFRGRGSGTQFTLTISSLQAEDSGTYFC***LQHNTYPLT***FGPGTKVEIKR |

Light chain variable region (VL) sequence of the developed antibody

TABLE 9

| SEQ ID NO | Name | Sequence |
|---|---|---|
| 56 | AG8 | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDRYGSGTYGFGMDV***WGPGTLVT |
| 57 | #1NNK | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDRYGSGTYFFGMDV***WGPGTLVT |
| 58 | #2NNK | EVQLVESGAEVRKPGASVKVSCKAS***GYTFTSS***DINWIRQATGQGLEWMGY***MNPKNGNT***DYAQKFQGRISMTRDSSISTAYMELSSMRSEDTAVYYC***AKDRYGSGTYQFGMDV***WGPGTLVT |
| 59 | #3NNK | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDRYGSGTIGFGMDV***WGPGTLVT |
| 60 | #4NNK | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDRYGSGTHGFGMDV***WGPGTLVT |
| 61 | #5NNK | EVQLVESGAEVRKPGASVKVSCKA***SGYTFTSS***DINWIRQATGQGLEWMGY***MNPKNGNT***DYAQKFQGRISMTRDSSISTAYMELSSLRSEDTAVYYC***AKDRYGSGTYGFNMDV***WGPGTLVT |
| 62 | #6NNK | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDRYGSGTYGFCMDV***WGPGTLVT |
| 63 | #7NNK | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDRYGSGTYGFGLDV***WGPGTLVT |
| 64 | EF12 | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDPYGSGTYGFGMDV***WGPGTLVT |
| 65 | GG12 | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDRYGSGVYGFGMDV***WGPGTLVT |
| 66 | FG12 | EVQLVESGAEVRKPGASVKVSCKAS***GYTFTSS***DINWIRQATGQGLEWMGY***MNPKNGNT***DYAQKFQGRISMTRDSSISTAYMELSSLRSEDTAVYYC***AKDRYGLGTYGFGMDV***WGPGTLVT |

TABLE 9-continued

| SEQ ID NO | Name | Sequence |
|---|---|---|
| 67 | AB9 | EVQLVESGAEVRKPGASVKVSCKASGYTFTSSDINWI RQATGQGLEWMGYMNPKNGNTDYAQKFQGRISMTRDS SISTAYMELSSLRSEDTAVYYCAKDRYGSGTYGEGMD VVWGPGTLVT |

Heavy chain variable region (VH) sequences of the developed antibodies

Figure 5:
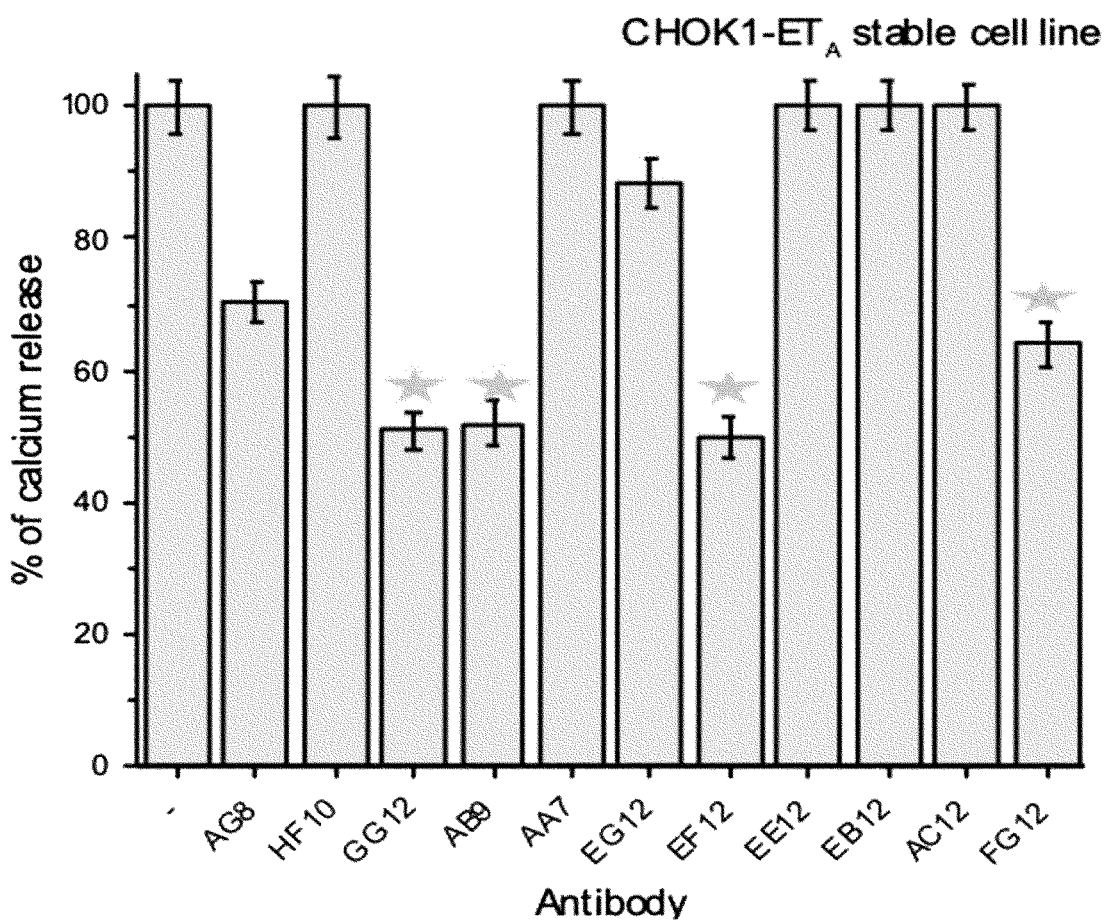
FIG. 5 shows the inhibitory activities of developed antibodies at a concentration of 200 nM for signaling induced by 10 nM ET-1 in $ET_A$-expressing animal cells (CHO-K1 cells).

<Example 3> Confirmation of Inhibitory Activities of the Developed $ET_A$-Specific Antibodies for Signaling Using Human-Derived $ET_A$-Expressing Animal Cells Intracytoplasmic $Ca^{2+}$ concentrations were measured using a fluorescent dye (Fura-2-AM, ThermoFisher, USA) to determine the signaling pathways of $ET_A$ by ET-1. Specifically, first, $10^5$ cells of an $ET_A$-expressing CHO-K1 stable cell line (GenScript, USA) were treated with 5 M1V Fura-2-AM fluorescent dye and different concentrations of each of the purified antibodies (FIG. 5). Then, signaling was induced with 10 nM ET-1. The emission by 340 nm excitation/emission by 380 nm excitation was determined at an emission wavelength of 510 nm using a fluorescence spectrophotometer (Biotek, USA) to analyze the intracytoplasmic $Ca^{2+}$ concentrations and elicit the inhibitory activities of the developed antibodies for intracellular $ET_A$ signaling.

Figure 6:
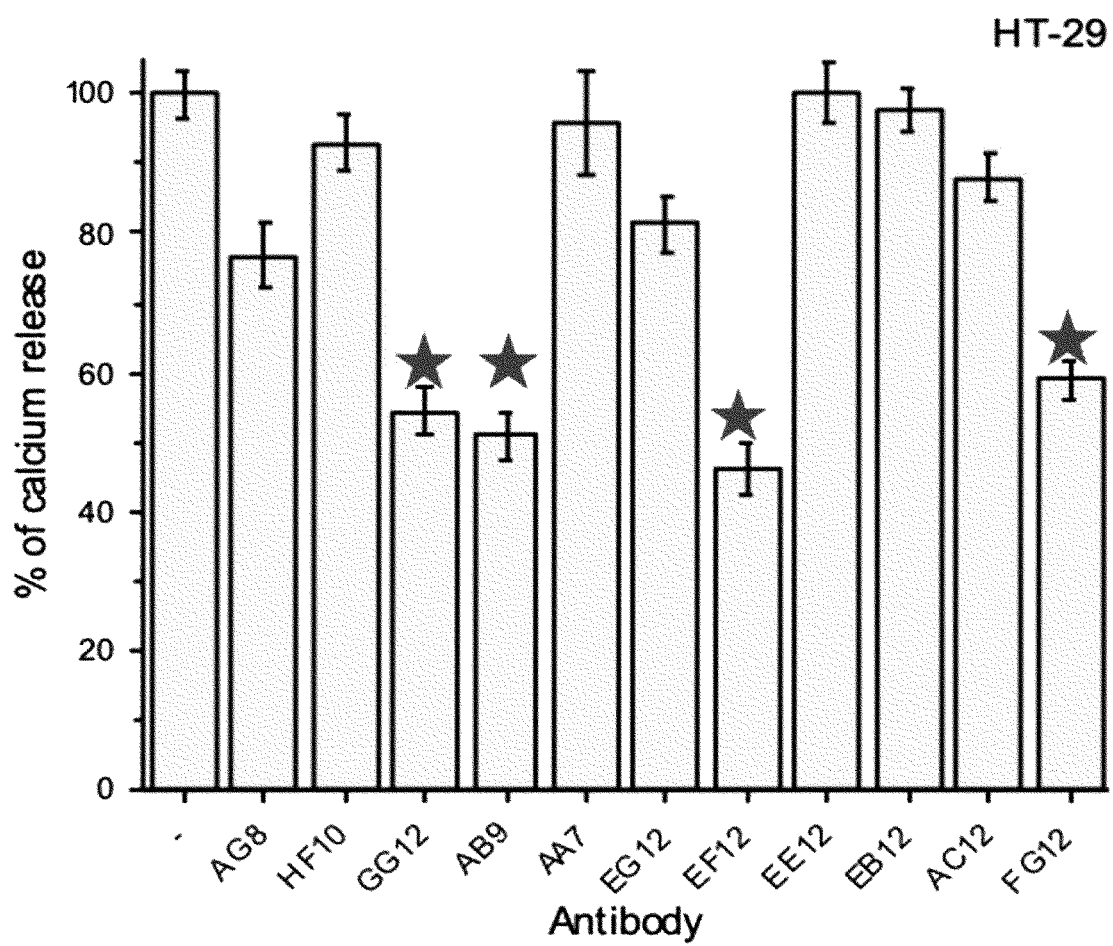
FIG. 6 shows the inhibitory activities of developed antibodies at a concentration of 200 nM for signaling induced by 10 nM ET-1 in $ET_A$-overexpressing cells of HT-29, a colorectal cancer cell line.
Figure 7:
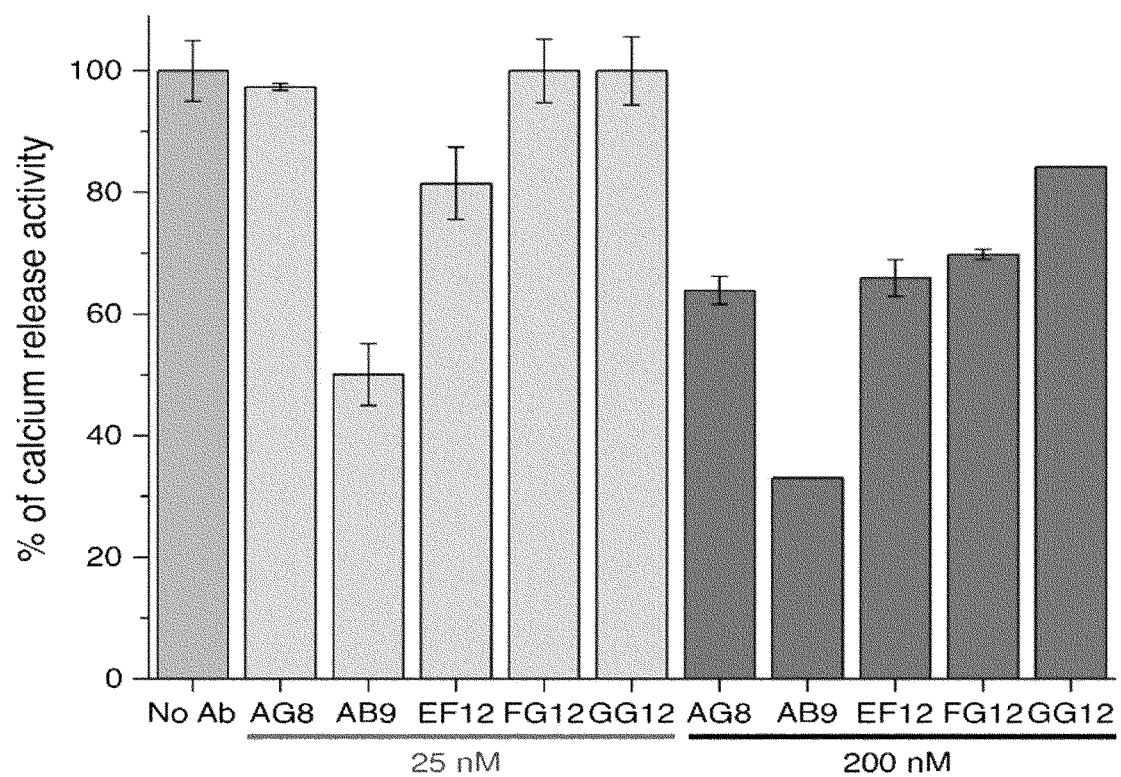
FIG. 7 shows the inhibitory activities of developed antibodies at concentrations of 25 nM and 200 nM for signaling induced by 10 nM ET-1 in $ET_A$-overexpressing cells of HCT-116, a colorectal cancer cell line.

<Example 4> Confirmation of Inhibitory Activities of the Developed $ET_A$-Specific Antibodies for $ET_A$ Signaling in Colorectal Cancer Cells and Selection of 5 Lead Antibodies Colorectal cancer cell lines HT-29 and HCT-116 procured from the Korea Cell Line Bank (Seoul, Korea) were used. The inhibitory activities of the developed antibodies for $ET_A$ signaling in the HT-29 colorectal cancer cells were confirmed in the same manner as in Example 3. The results are shown in FIG. 6. The inhibitory activities of the developed antibodies for $ET_A$ signaling in HCT-116 colorectal cancer cells were confirmed by treatment of the developed antibodies at concentrations of 25 nM and 200 nM under the same conditions as described in Example 3. The results are shown in FIG. 7. Referring to FIGS. 6 and 7, the developed antibodies showed antagonistic effects to inhibit $ET_A$ signaling by ET-1 in the colorectal cancer cell lines HT-29 and HCT-116. Among the developed antibodies, four (GG12, AB9, EF12, and FG12) were finally selected that showed inhibitory activities for signaling induced by $ET_A$ activity in both human-derived $ET_A$-expressing cells and overexpressing HT-29 and HCT-116 cancer cells (see FIGS. 5, 6, and 7).

<Example 5> Confirmation of Cross-Binding Activities of the 5 Lead Antibodies to Human $ET_A$ and Mouse $ET_A$ For drug development using the lead antibodies (AG8, AB9, EF12, FG12, and GG12), the sequence of the extracellular domain of human $ET_A$ was compared with those of other species to select an appropriate animal model. As a result, the N-terminal region and extracellular loops 1, 2, and 3 of mouse $ET_A$ were analyzed to have an amino acid sequence identity of ≥~80% on average with those of human $ET_A$. Based on this result, the mouse $ET_A$ sequence was cloned into an expression vector and active mouse $ET_A$ was expressed and purified in the presence of *E. coli*, as described in Korean Patent No. 10-2014383. The cross-binding activities of the developed antibodies to human $ET_A$ and mouse $ET_A$ were tested by ELISA. The results are shown in FIG. 8.

Figure 8:
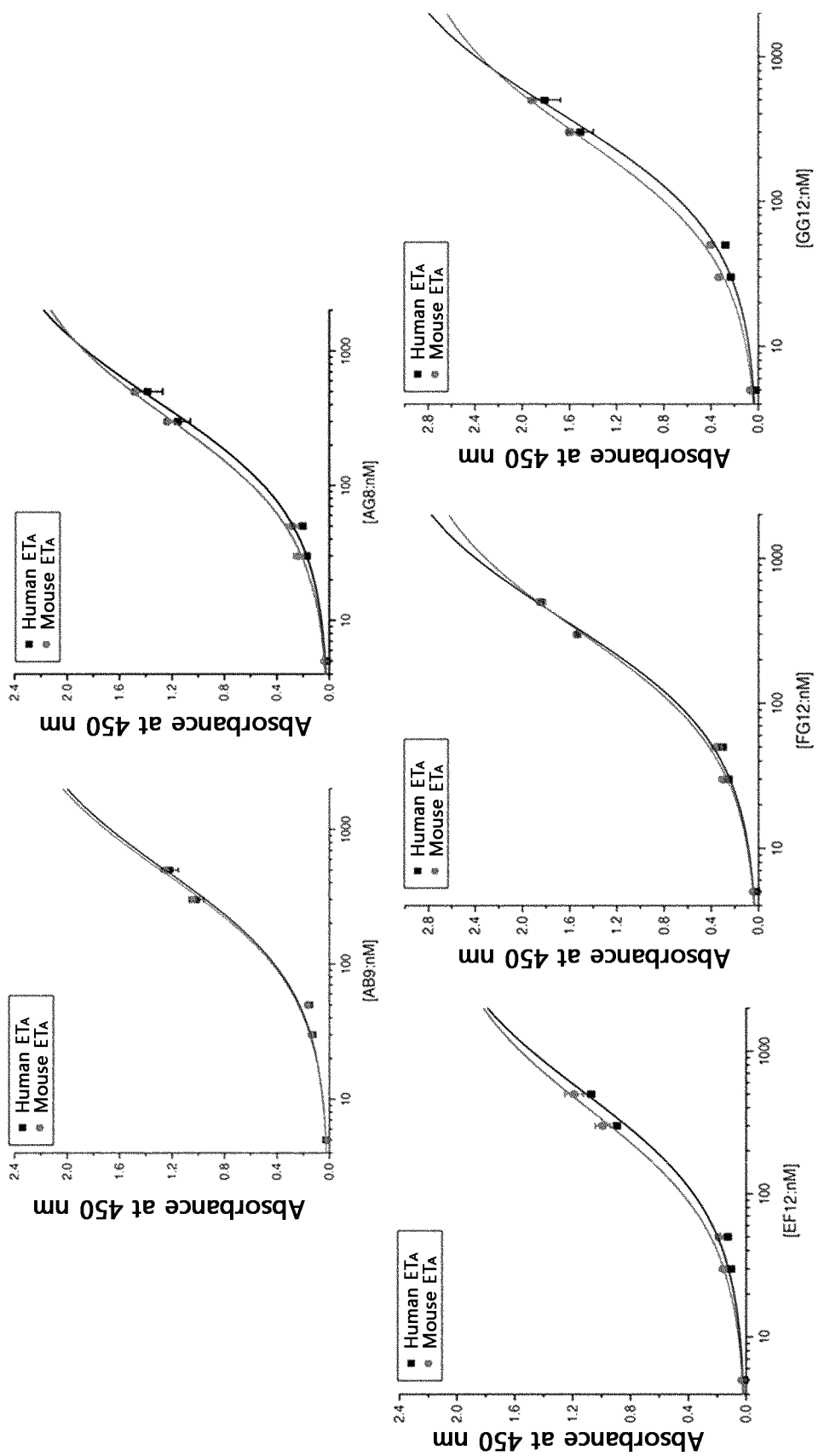
FIG. 8 shows the cross-binding activities of 5 lead antibodies to active human $ET_A$ and mouse $ET_A$.

Referring to FIG. 8, the binding activities of the developed antibodies to active human $ET_A$ were similar to those to active mouse $ET_A$.

Figure 9:
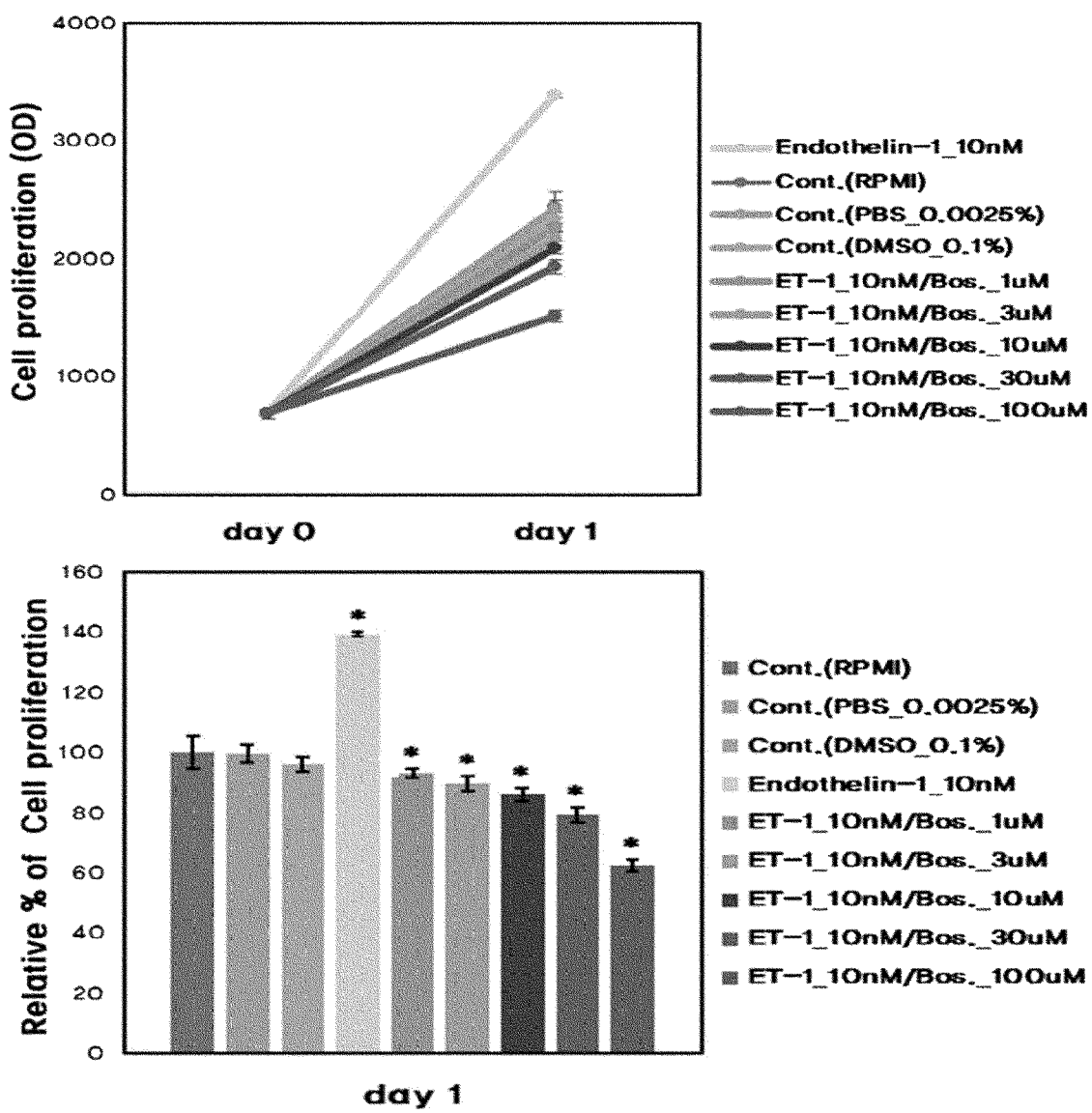
FIG. 9 shows the inhibitory effect of a developed antibody on the proliferation of $ET_A$-overexpressing colorectal cancer cells of HCT-116 line.
Figure 10:
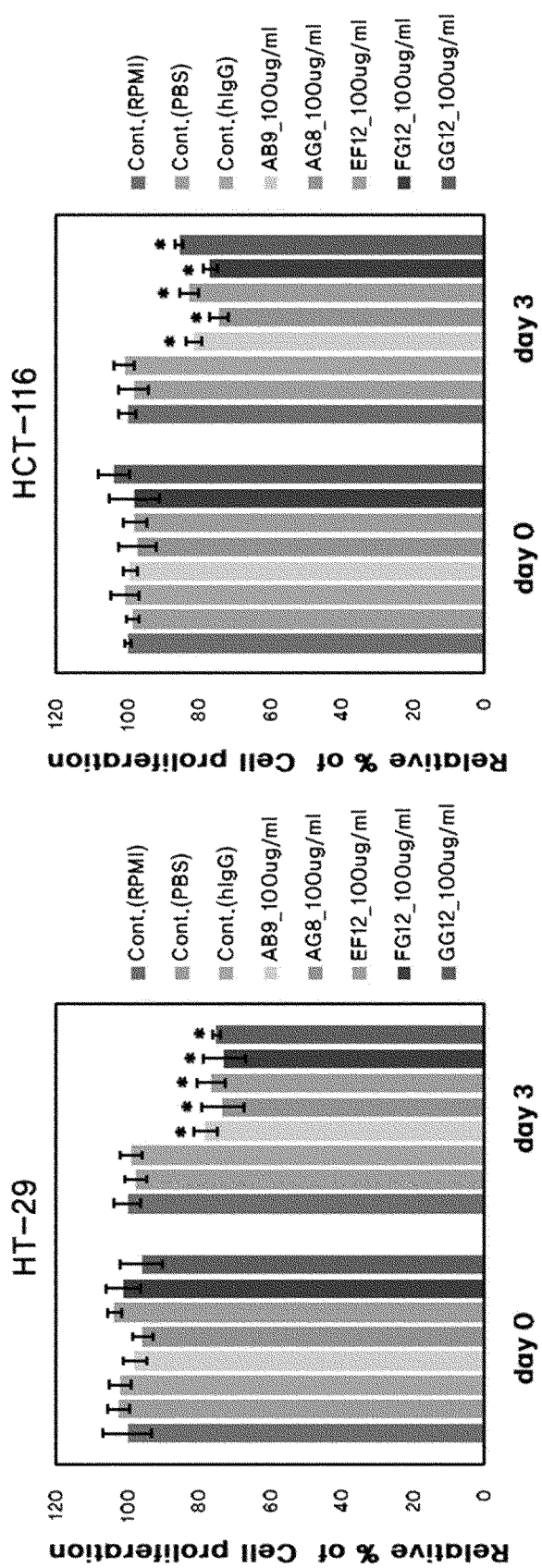
FIG. 10 shows the inhibitory effects of 5 lead antibodies on the proliferation of $ET_A$-overexpressing colorectal cancer cells of HT-29 and HCT-116 lines.

<Example 6> Confirmation of Inhibitory Activities of the Developed Lead Antibodies on Proliferation of Colorectal Cancer Cells In this example, a determination was made as to whether the developed antibodies had inhibitory activities on the proliferation of colorectal cancer cells of HCT-116 line, which is widely used as much as HT-29 line, even in the presence of ET-1. The amount of DNA in cells was measured using a fluorescent dye (CyQUANT NF, Invitrogen, USA) to determine the degree of proliferation of the cells. The HCT-116 cell line was treated with different concentrations of the developed antibodies and cultured in a cell incubator at 37° C. for 1 h. 72 h after inoculation, the cells were treated with a fluorescent dye (CyQUANT NF) and the emission by 485 nm excitation was measured using a fluorescence spectrophotometer (TECAN, Switzerland) to determine the amount of DNA in the cells. It was determined from the DNA amount whether the developed antibodies were bound to extracellular domain of $ET_A$ to inhibit the proliferation of the colorectal cancer cells. The results are shown in FIG. 9. Referring to FIG. 9, the inventive antibody had an inhibitory effect on an increase in the proliferative capacity of $ET_A$ by ET-1 in the HCT-116 colorectal cancer cell line. These results reveal that the inventive antibody has an inhibitory activity for the proliferation of colorectal cancer cells. The abilities of the 5 lead antibodies to inhibit the proliferation of HT-29 and HCT-116 colorectal cancer cell lines were confirmed by the same method as described in Example 6. The results as shown in FIG. 10. Referring to FIG. 10, the 5 lead antibodies showed inhibitory effects on the proliferation of the HT-29 and HCT-116 colorectal cancer cell lines. These results demonstrate that the 5 lead antibodies have inhibitory activities for the proliferation of colorectal cancer cells.

Figure 11:
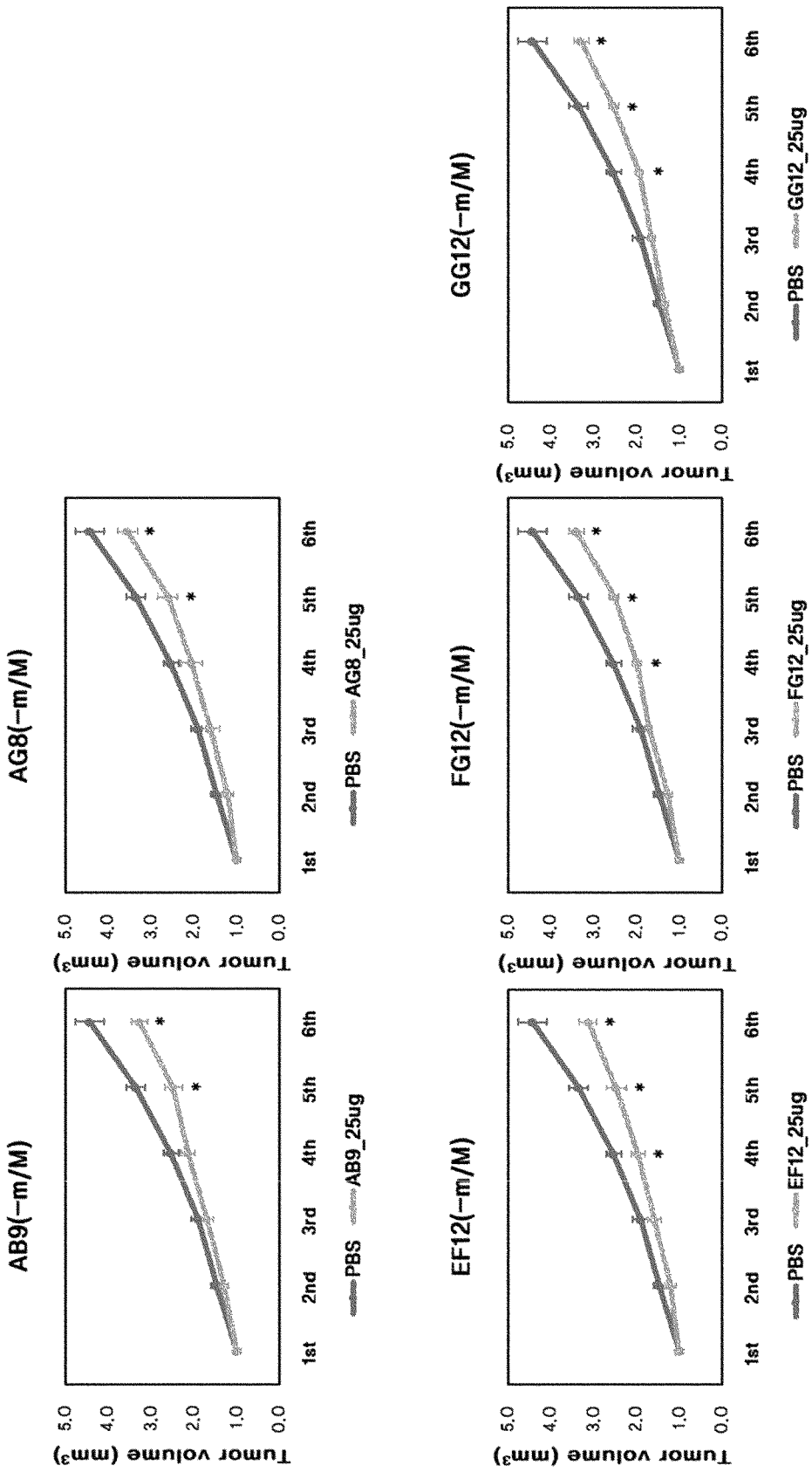
FIG. 11 shows the inhibitory effects of 5 lead antibodies on the growth of colorectal cancer in xenograft models established from the colorectal cancer cell line HT-29.

<Example 7> Validation of Anticancer Activities of the 5 Developed Lead Antibodies in Colorectal Cancer Animal Models The colorectal cancer cell line HT-29 was injected subcutaneously into the flank region of BALB/c nude mice to establish xenograft models. 25 μg of each of the 5 lead antibodies was injected to validate its anticancer activity. The results are shown in FIG. 11. Referring to FIG. 11, the 5 lead antibodies showed inhibitory effects on the growth of colorectal cancer in the xenograft models of the HT-29 colorectal cancer cell line. These results demonstrate that the 5 lead antibodies have inhibitory activities for the proliferation of colorectal cancer cells even in animal models, thus being suitable for use in therapeutic agents.

Figure 12:
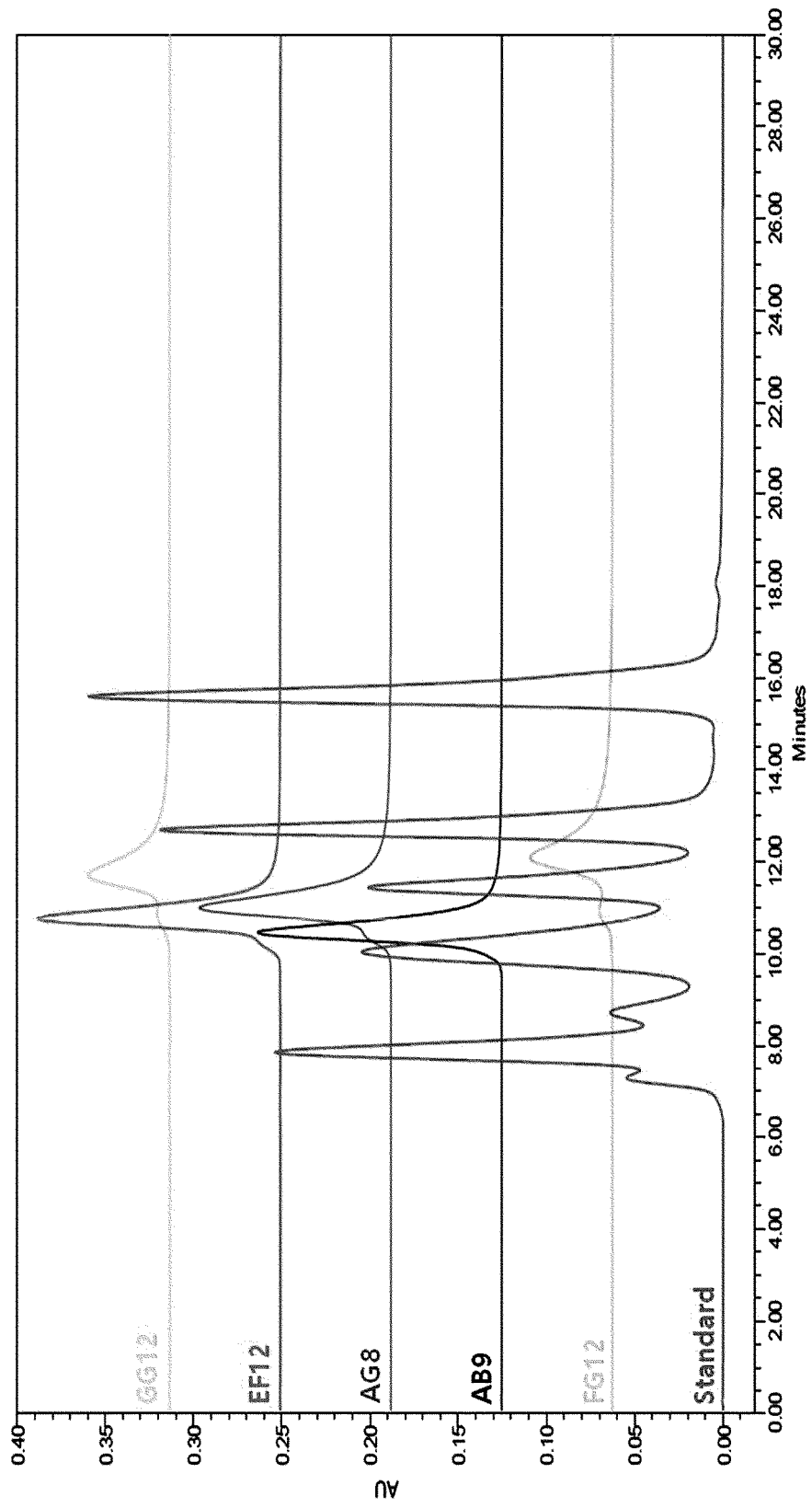
FIG. 12 shows the results of size-exclusion chromatography (SEC)-HPLC for 5 lead antibodies.
Figure 13:
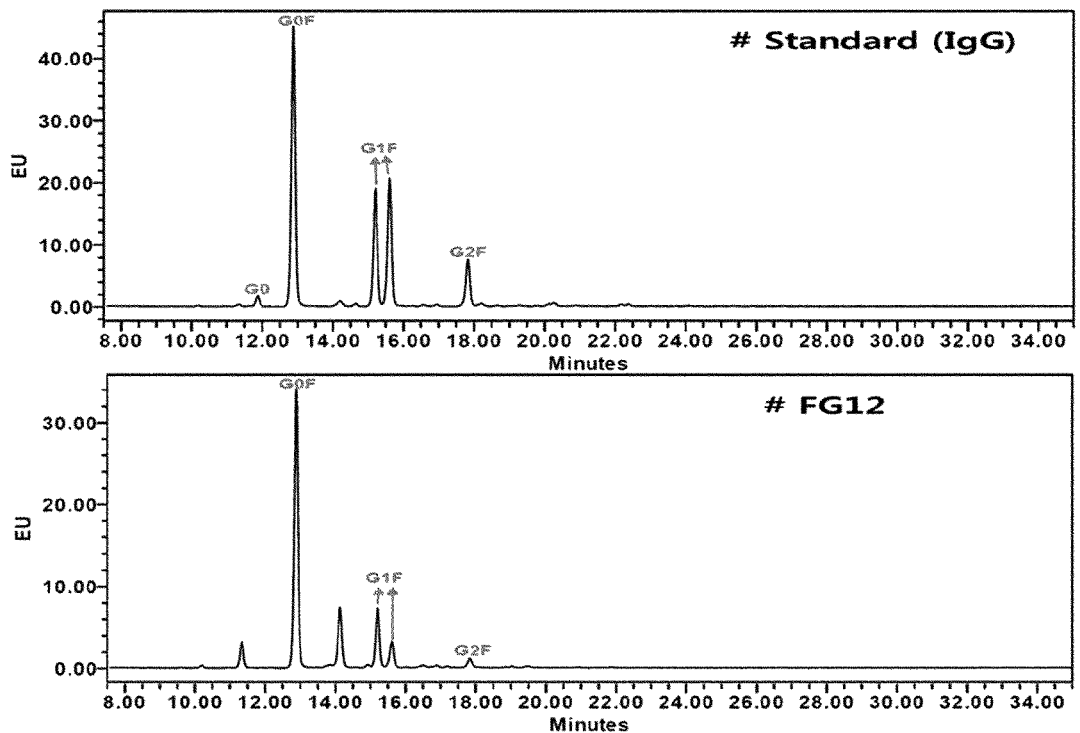
FIG. 13 shows the results of N-glycan profiling for 5 lead antibodies.
Figure 14:
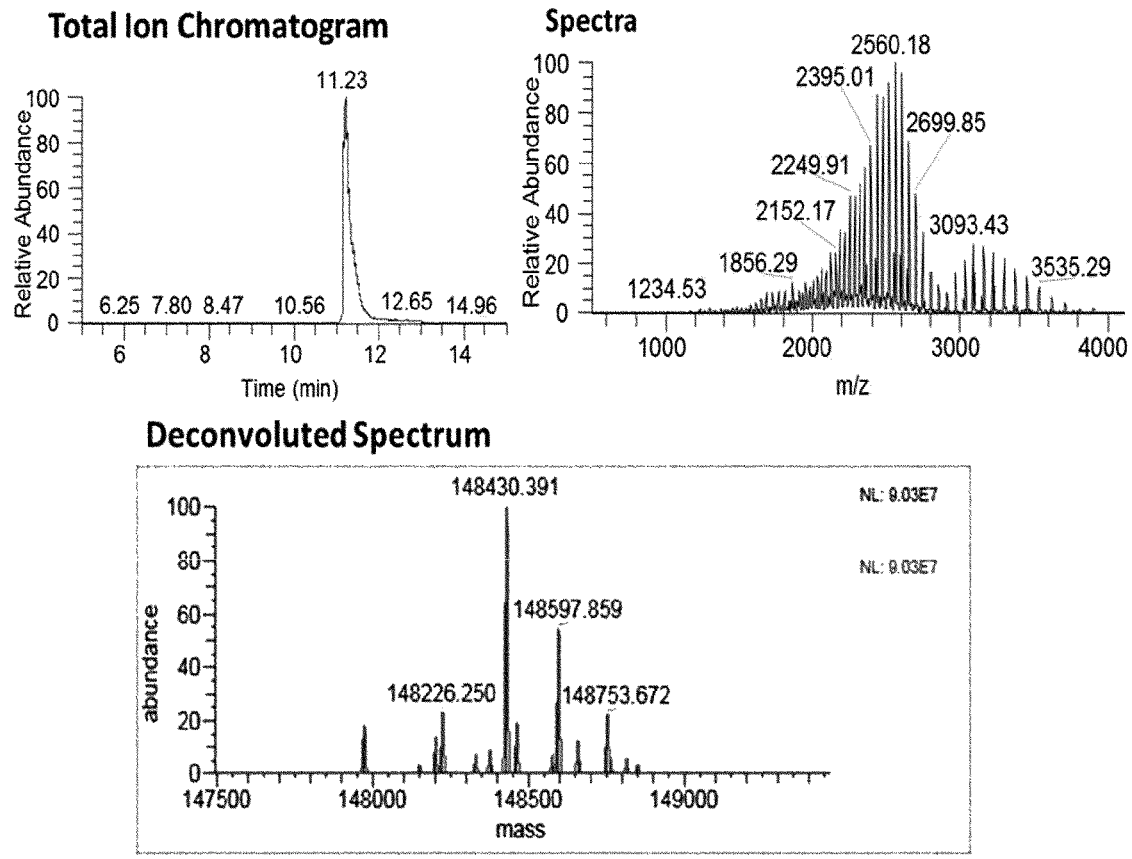
FIG. 14 shows the results of mass analysis for 5 lead antibodies.

<Example 8> Validation of Anticancer Activities of the 5 Developed Lead Antibodies in Colorectal Cancer Animal Model As shown in FIG. 12, the aggregation rates (%) of the 5 developed antibodies were found to be as low as ≤10% when separated by SEC-HPLC. N-glycan profiling of the developed antibodies was performed. As a result, the N-glycan profiles of the developed antibodies were not significantly different from that of human IgG standard, as shown in FIG. 13. It was analyzed whether the sizes of the developed antibodies were consistent with their theoretical values. The results are shown in FIG. 14. Referring to FIG. 14, the sizes of the developed antibodies were almost consistent with the sequence sizes within 5 Da.

Figure 15:
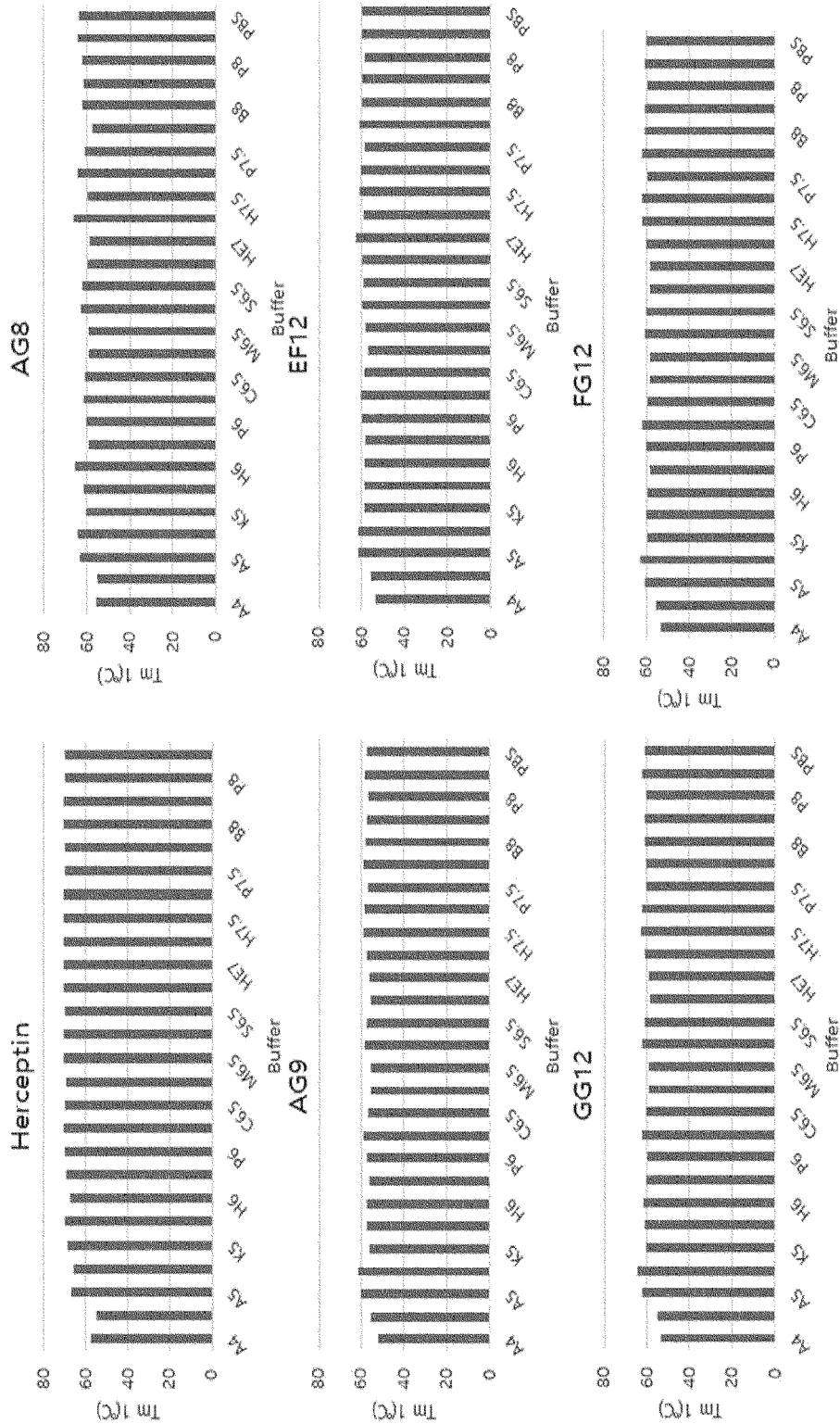
FIG. 15 shows the results of thermal stability analysis for 5 lead antibodies.

The thermal stabilities of the 5 developed antibodies were determined for buffer exchange. To this end, different buffers at pH 4-8 (sodium acetate, sodium citrate, potassium phosphate, histidine, MES, succinate, HEPES, Tris, bicine, and PBS) were used. After buffer exchange, each of the antibodies was concentrated to 1 mg/mL and diluted to a final concentration of 1× with a 1000× protein thermal shift™ dye (ThermoFisher scientific), which can be used to predict structural changes of the protein. Thermal stability analysis was performed using ViiA7 (ThermoFisher scientific) according to the manufacturer's manual (Protein Thermal™ Studies, ThermoFisher scientific). The pH-dependent thermal stabilities are shown in FIG. 15.

Figure 16:
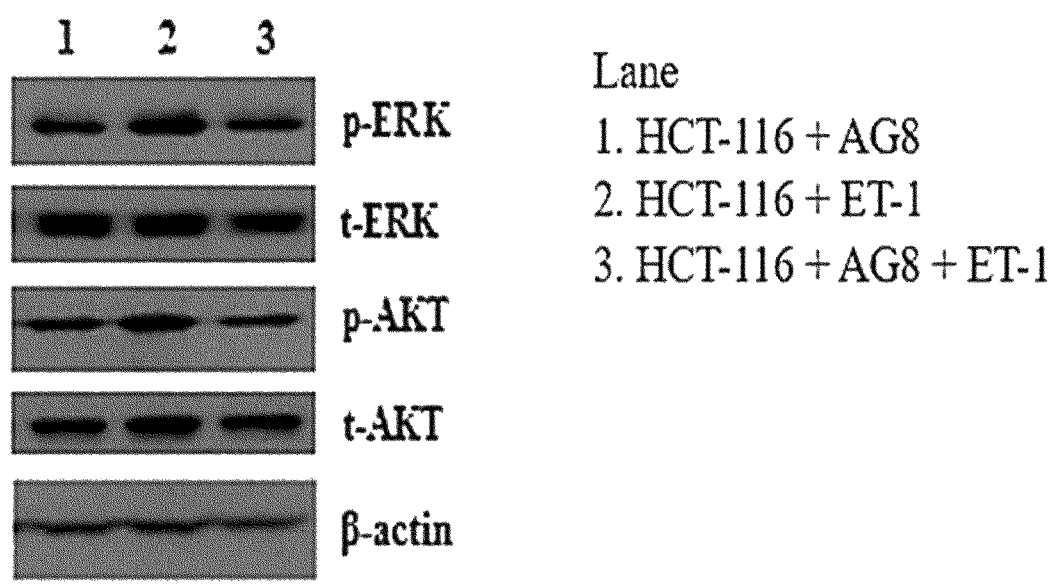
FIG. 16 shows reductions in the level of ERK and AKT as products of $ET_A$ signaling pathways by treatment with a developed antibody.

<Example 9> Determination of Mechanism of Inhibition of $ET_A$ Signaling by the 5 Developed Lead Antibodies in Colorectal Cancer Cells The inhibitory activities of the developed antibodies for $ET_A$ signaling in HCT-116 colorectal cancer cells were confirmed by immunoblot assay for phosphorylation of ERK and AKT proteins as final active products of $ET_A$ signaling pathways. The results are shown in FIG. 16. Referring to FIG. 16, the inventive antibody showed an antagonistic effect to inhibit phosphorylation of ERK and AKT proteins as final active products of $ET_A$ signaling by ET-1 in the colorectal cancer cell line HCT-116. These results demonstrate that the developed antibodies have inhibitory activities for $ET_A$ signaling.

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

We claim:

1. A monoclonal antibody or a fragment thereof that recognizes and binds specifically to endothelin receptor type A or its extracellular domain as an antigen wherein the monoclonal antibody or fragment thereof comprises a heavy chain variable region comprising a CDR1 of SEQ ID NO: 38 and a CDR2 of SEQ ID NO: 39 and a light chain variable region comprising a CDR1 of SEQ ID NO: 40, a CDR2 of SEQ ID NO: 41, and a CDR3 of SEQ ID NO: 42 and wherein the CDR3 of the heavy chain variable region comprises the amino acid sequence of SEQ ID NO: 43 or a mutation selected from the group consisting of: a substitution of the amino acid at position 4 in the sequence of SEQ ID NO: 43 to proline (P), a substitution of the amino acid at position 7 in the sequence of SEQ ID NO: 43 to leucine (L), a substitution of the amino acid at position 9 in the sequence of SEQ ID NO: 43 to valine (V), a substitution of the amino acid at position 10 in the sequence of SEQ ID NO: 43 to isoleucine (I) or histidine (H), a substitution of the amino acid at position 11 in the sequence of SEQ ID NO: 43 to phenylalanine (F) or glutamine (Q), a substitution of the amino acid at position 12 in the sequence of SEQ ID NO: 43 to glutamate (E), a substitution of the amino acid at position 13 in the sequence of SEQ ID NO: 43 to asparagine (N) or cysteine (C) or a substitution of the amino acid at position 14 in the sequence of SEQ ID NO: 43 to leucine (L).

2. The monoclonal antibody or fragment thereof according to claim 1, wherein the CDR3 of the heavy chain variable region comprises the amino acid sequence selected from the group consisting of the amino acid sequences of SEQ ID NOs: 44-54.

3. The monoclonal antibody or fragment thereof according to claim 1, wherein the light chain variable region comprises the amino acid sequence of SEQ ID NO: 55.

4. The monoclonal antibody or fragment thereof according to claim 1, wherein the heavy chain variable region comprises the amino acid sequence selected from the group consisting of the amino acid sequences of SEQ ID NOs: 56-67.

5. The monoclonal antibody or fragment thereof according to claim 1, wherein the endothelin receptor type A comprises the amino acid sequence of SEQ ID NO: 68.

6. The monoclonal antibody or fragment thereof according to claim 1, wherein the extracellular domain comprises one or more domains selected from the group consisting of N-term of SEQ ID NO: 69, ECL1 of SEQ ID NO: 70, ECL2 of SEQ ID NO: 71, and ECL3 of SEQ ID NO: 72.

7. A nucleic acid molecule encoding the monoclonal antibody or fragment thereof according to claim 1.

8. A vector comprising the nucleic acid molecule according to claim 7.

9. A host cell comprising the vector according to claim 8.

10. A pharmaceutical composition for preventing or treating cancer comprising the monoclonal antibody or fragment thereof according to claim 1.

11. A pharmaceutical composition for preventing or treating hypertension comprising the monoclonal antibody or fragment thereof according to claim 1.

12. A method for treating cancer or hypertension comprising administering to a subject a pharmaceutically effective amount of the monoclonal antibody or fragment thereof according to claim 1.

13. A method of making a pharmaceutical composition for treating cancer or hypertension, comprising:
providing a monoclonal antibody or fragment thereof according to claim 1, a nucleic acid molecule encoding the monoclonal antibody or fragment thereof or a vector comprising the nucleic acid molecule.

14. A method for quantifying endothelin receptor type A in a sample, comprising treating the sample with the monoclonal antibody or fragment thereof according to claim 1.

15. A method for providing information regarding the expression of endothelin receptor type A, comprising (a) separating a sample from a subject, (b) treating the sample with the monoclonal antibody or fragment thereof according to claim 1, and (c) determining whether the expression level of endothelin receptor type A in the sample from the subject is higher than that of endothelin receptor type A in a normal sample.

16. The method according to claim 15, wherein the disease caused by overexpression of endothelin receptor type A is cancer or hypertension.

17. A kit for quantifying endothelin receptor type A comprising the monoclonal antibody or fragment thereof according to claim 1.

* * * * *

SEQUENCE LISTING

<160> NUMBER OF SEQ ID NOS: 73

<210> SEQ ID NO 1
<211> LENGTH: 88
<212> TYPE: DNA
<213> ORGANISM: Artificial Sequence
<220> FEATURE:
<223> OTHER INFORMATION: AG8-CDR3H-NNK1-RV
<220> FEATURE:
<221> NAME/KEY: misc_feature
<222> LOCATION: (54)..(55)
<223> OTHER INFORMATION: n is a, c, g, or t

<400> SEQUENCE: 1
gggttcccgg gccccagacg tccataccga agccataagt ccccgaacca tamnnatctt    60
ttgcacagta atacacggcc gtgtcctc                                        88

<210> SEQ ID NO 2
<211> LENGTH: 88
<212> TYPE: DNA
<213> ORGANISM: Artificial Sequence
<220> FEATURE:
<223> OTHER INFORMATION: AG8-CDR3H-NNK2-RV
<220> FEATURE:
<221> NAME/KEY: misc_feature
<222> LOCATION: (51)..(52)
<223> OTHER INFORMATION: n is a, c, g, or t

<400> SEQUENCE: 2
gggttcccgg gccccagacg tccataccga agccataagt ccccgaaccm nncctatctt    60
ttgcacagta atacacggcc gtgtcctc                                        88

<210> SEQ ID NO 3
<211> LENGTH: 88
<212> TYPE: DNA
<213> ORGANISM: Artificial Sequence
<220> FEATURE:
<223> OTHER INFORMATION: AG8-CDR3H-NNK3-RV
<220> FEATURE:
<221> NAME/KEY: misc_feature
<222> LOCATION: (48)..(49)
<223> OTHER INFORMATION: n is a, c, g, or t

<400> SEQUENCE: 3
gggttcccgg gccccagacg tccataccga agccataagt ccccgamnna tacctatctt    60
ttgcacagta atacacggcc gtgtcctc                                       88

<210> SEQ ID NO 4
<211> LENGTH: 88
<212> TYPE: DNA
<213> ORGANISM: Artificial Sequence
<220> FEATURE:
<223> OTHER INFORMATION: AG8-CDR3H-NNK4-RV
<220> FEATURE:
<221> NAME/KEY: misc_feature
<222> LOCATION: (45)..(46)
<223> OTHER INFORMATION: n is a, c, g, or t

<400> SEQUENCE: 4
gggttcccgg gccccagacg tccataccga agccataagt cccmnnacca tacctatctt    60
ttgcacagta atacacggcc gtgtcctc                                       88

<210> SEQ ID NO 5
<211> LENGTH: 88
<212> TYPE: DNA
<213> ORGANISM: Artificial Sequence
<220> FEATURE:
<223> OTHER INFORMATION: AG8-CDR3H-NNK5-RV
<220> FEATURE:
<221> NAME/KEY: misc_feature
<222> LOCATION: (42)..(43)
<223> OTHER INFORMATION: n is a, c, g, or t

<400> SEQUENCE: 5
gggttcccgg gccccagacg tccataccga agccataagt mnncgaacca tacctatctt    60
ttgcacagta atacacggcc gtgtcctc                                       88

<210> SEQ ID NO 6
<211> LENGTH: 88
<212> TYPE: DNA
<213> ORGANISM: Artificial Sequence
<220> FEATURE:
<223> OTHER INFORMATION: AG8-CDR3H-NNK6-RV
<220> FEATURE:
<221> NAME/KEY: misc_feature
<222> LOCATION: (39)..(40)
<223> OTHER INFORMATION: n is a, c, g, or t

<400> SEQUENCE: 6
gggttcccgg gccccagacg tccataccga agccatamnn ccccgaacca tacctatctt    60
ttgcacagta atacacggcc gtgtcctc                                       88

<210> SEQ ID NO 7
<211> LENGTH: 88
<212> TYPE: DNA
<213> ORGANISM: Artificial Sequence
<220> FEATURE:
<223> OTHER INFORMATION: AG8-CDR3H-NNK7-RV
<220> FEATURE:
<221> NAME/KEY: misc_feature
<222> LOCATION: (36)..(37)
<223> OTHER INFORMATION: n is a, c, g, or t

<400> SEQUENCE: 7
gggttcccgg gccccagacg tccataccga agccmnnagt ccccgaacca tacctatctt    60
ttgcacagta atacacggcc gtgtcctc                                       88

<210> SEQ ID NO 8

```
<211> LENGTH: 88
<212> TYPE: DNA
<213> ORGANISM: Artificial Sequence
<220> FEATURE:
<223> OTHER INFORMATION: AG8-CDR3H-NNK8-RV
<220> FEATURE:
<221> NAME/KEY: misc_feature
<222> LOCATION: (33)..(34)
<223> OTHER INFORMATION: n is a, c, g, or t

<400> SEQUENCE: 8
gggttcccgg gccccagacg tccataccga amnnataagt ccccgaacca tacctatctt    60
ttgcacagta atacacggcc gtgtcctc                                       88

<210> SEQ ID NO 9
<211> LENGTH: 88
<212> TYPE: DNA
<213> ORGANISM: Artificial Sequence
<220> FEATURE:
<223> OTHER INFORMATION: AG8-CDR3H-NNK9-RV
<220> FEATURE:
<221> NAME/KEY: misc_feature
<222> LOCATION: (30)..(31)
<223> OTHER INFORMATION: n is a, c, g, or t

<400> SEQUENCE: 9
gggttcccgg gccccagacg tccataccmn ngccataagt ccccgaacca tacctatctt    60
ttgcacagta atacacggcc gtgtcctc                                       88

<210> SEQ ID NO 10
<211> LENGTH: 88
<212> TYPE: DNA
<213> ORGANISM: Artificial Sequence
<220> FEATURE:
<223> OTHER INFORMATION: CDR3H-NNK10-RV
<220> FEATURE:
<221> NAME/KEY: misc_feature
<222> LOCATION: (27)..(28)
<223> OTHER INFORMATION: n is a, c, g, or t

<400> SEQUENCE: 10
gggttcccgg gccccagacg tccatmnnga agccataagt ccccgaacca tacctatctt    60
ttgcacagta atacacggcc gtgtcctc                                       88

<210> SEQ ID NO 11
<211> LENGTH: 88
<212> TYPE: DNA
<213> ORGANISM: Artificial Sequence
<220> FEATURE:
<223> OTHER INFORMATION: AG8-CDR3H-NNK11-RV
<220> FEATURE:
<221> NAME/KEY: misc_feature
<222> LOCATION: (24)..(25)
<223> OTHER INFORMATION: n is a, c, g, or t

<400> SEQUENCE: 11
gggttcccgg gccccagacg tcmnnaccga agccataagt ccccgaacca tacctatctt    60
ttgcacagta atacacggcc gtgtcctc                                       88

<210> SEQ ID NO 12
<211> LENGTH: 88
<212> TYPE: DNA
<213> ORGANISM: Artificial Sequence
<220> FEATURE:
<223> OTHER INFORMATION: AG8-CDR3H-NNK12-RV
<220> FEATURE:
<221> NAME/KEY: misc_feature
```

```
<222> LOCATION: (21)..(22)
<223> OTHER INFORMATION: n is a, c, g, or t

<400> SEQUENCE: 12
gggttcccgg gccccagacm nncataccga agccataagt ccccgaacca tacctatctt    60
ttgcacagta atacacggcc gtgtcctc                                        88

<210> SEQ ID NO 13
<211> LENGTH: 88
<212> TYPE: DNA
<213> ORGANISM: Artificial Sequence
<220> FEATURE:
<223> OTHER INFORMATION: AG8-CDR3H-NNK13-RV
<220> FEATURE:
<221> NAME/KEY: misc_feature
<222> LOCATION: (18)..(19)
<223> OTHER INFORMATION: n is a, c, g, or t

<400> SEQUENCE: 13
gggttcccgg ccccamnng tccataccga agccataagt ccccgaacca tacctatctt     60
ttgcacagta atacacggcc gtgtcctc                                        88

<210> SEQ ID NO 14
<211> LENGTH: 123
<212> TYPE: PRT
<213> ORGANISM: Artificial Sequence
<220> FEATURE:
<223> OTHER INFORMATION: #1NNK

<400> SEQUENCE: 14

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Phe Phe Gly Met Asp Val
            100                 105                 110

Trp Gly Pro Gly Thr Leu Val Thr Val Ser Ser
        115                 120

<210> SEQ ID NO 15
<211> LENGTH: 123
<212> TYPE: PRT
<213> ORGANISM: Artificial Sequence
<220> FEATURE:
<223> OTHER INFORMATION: #2NNK

<400> SEQUENCE: 15

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45
```

Gly Tyr Met Asn Pro Lys Asn Gly Asn Thr Asp Tyr Ala Gln Lys Phe
            50                  55                  60

Gln Gly Arg Ile Ser Met Thr Arg Asp Ser Ser Ile Ser Thr Ala Tyr
 65                  70                  75                  80

Met Glu Leu Ser Ser Met Arg Ser Glu Asp Thr Ala Val Tyr Tyr Cys
                 85                  90                  95

Ala Lys Asp Arg Tyr Gly Ser Gly Thr Tyr Gln Phe Gly Met Asp Val
                100                 105                 110

Trp Gly Pro Gly Thr Leu Val Thr Val Ser Ser
            115                 120

<210> SEQ ID NO 16
<211> LENGTH: 123
<212> TYPE: PRT
<213> ORGANISM: Artificial Sequence
<220> FEATURE:
<223> OTHER INFORMATION: #3NNK

<400> SEQUENCE: 16

Glu Val Gln Leu Val Glu Ser Gly Ala Glu Val Arg Lys Pro Gly Ala
 1               5                  10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
                35                  40                  45

Gly Tyr Met Asn Pro Lys Asn Gly Asn Thr Asp Tyr Ala Gln Lys Phe
            50                  55                  60

Gln Gly Arg Ile Ser Met Thr Arg Asp Ser Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Asp Arg Tyr Gly Ser Gly Thr Ile Gly Phe Gly Met Asp Val
                100                 105                 110

Trp Gly Pro Gly Thr Leu Val Thr Val Ser Ser
            115                 120

<210> SEQ ID NO 17
<211> LENGTH: 123
<212> TYPE: PRT
<213> ORGANISM: Artificial Sequence
<220> FEATURE:
<223> OTHER INFORMATION: #4NNK

<400> SEQUENCE: 17

Glu Val Gln Leu Val Glu Ser Gly Ala Glu Val Arg Lys Pro Gly Ala
 1               5                  10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
                35                  40                  45

Gly Tyr Met Asn Pro Lys Asn Gly Asn Thr Asp Tyr Ala Gln Lys Phe
            50                  55                  60

Gln Gly Arg Ile Ser Met Thr Arg Asp Ser Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Asp Arg Tyr Gly Ser Gly Thr His Gly Phe Gly Met Asp Val

```
                       100                 105                 110

Trp Gly Pro Gly Thr Leu Val Thr Val Ser Ser
        115                 120

<210> SEQ ID NO 18
<211> LENGTH: 123
<212> TYPE: PRT
<213> ORGANISM: Artificial Sequence
<220> FEATURE:
<223> OTHER INFORMATION: #5NNK

<400> SEQUENCE: 18

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Phe Asn Met Asp Val
            100                 105                 110

Trp Gly Pro Gly Thr Leu Val Thr Val Ser Ser
        115                 120

<210> SEQ ID NO 19
<211> LENGTH: 123
<212> TYPE: PRT
<213> ORGANISM: Artificial Sequence
<220> FEATURE:
<223> OTHER INFORMATION: #6NNK

<400> SEQUENCE: 19

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Phe Cys Met Asp Val
            100                 105                 110

Trp Gly Pro Gly Thr Leu Val Thr Val Ser Ser
        115                 120

<210> SEQ ID NO 20
<211> LENGTH: 123
<212> TYPE: PRT
<213> ORGANISM: Artificial Sequence
<220> FEATURE:
```

<223> OTHER INFORMATION: #7NNK

<400> SEQUENCE: 20

Glu Val Gln Leu Val Glu Ser Gly Ala Glu Val Arg Lys Pro Gly Ala
1               5                   10                  15
Ser Val Lys Val Ser Cys Lys Ala Ser Gly Tyr Thr Phe Thr Ser Ser
            20                  25                  30
Asp Ile Asn Trp Ile Arg Gln Ala Thr Gly Gln Gly Leu Glu Trp Met
        35                  40                  45
Gly Tyr Met Asn Pro Lys Asn Gly Asn Thr Asp Tyr Ala Gln Lys Phe
    50                  55                  60
Gln Gly Arg Ile Ser Met Thr Arg Asp Ser Ser Ile Ser Thr Ala Tyr
65                  70                  75                  80
Met Glu Leu Ser Ser Leu Arg Ser Glu Asp Thr Ala Val Tyr Tyr Cys
                85                  90                  95
Ala Lys Asp Arg Tyr Gly Ser Gly Thr Tyr Gly Phe Gly Leu Asp Val
            100                 105                 110
Trp Gly Pro Gly Thr Leu Val Thr Val Ser Ser
        115                 120

<210> SEQ ID NO 21
<211> LENGTH: 369
<212> TYPE: DNA
<213> ORGANISM: Artificial Sequence
<220> FEATURE:
<223> OTHER INFORMATION: #1NNK

<400> SEQUENCE: 21
gaggtgcagc tggtggagtc tggggctgag gtgaggaagc ctggggcctc agtgaaggtc    60
tcctgcaagg cttctggata caccttcacc agttctgata tcaactggat tcgacaggcc   120
actggacaag gcttgagtg atgggatac atgaaccta aaaatggaaa cacagactat   180
gcacagaagt tccagggcag aatctccatg accaggaca gctccataag cacagcctac   240
atggagctga gcagcctgag atctgaggac acggccgtgt attactgtgc aaaagatagg   300
tatggttcgg ggacttattt tttcggtatg gacgtctggg gcccgggaac cctggtcacc   360
gtctcctca                                                           369

<210> SEQ ID NO 22
<211> LENGTH: 369
<212> TYPE: DNA
<213> ORGANISM: Artificial Sequence
<220> FEATURE:
<223> OTHER INFORMATION: #2NNK

<400> SEQUENCE: 22
gaggtgcagc tggtggagtc tggggctgag gtgaggaagc ctggggcctc agtgaaggtc    60
tcctgcaagg cttctggata caccttcacc agttctgata tcaactggat tcgacaggcc   120
actggacaag gcttgagtg atgggatac atgaaccta aaaatggaaa cacagactat   180
gcacagaagt tccagggcag aatctccatg accaggaca gctccataag cacagcctac   240
atggagctga gcagcatgag atctgaggac acggccgtgt attactgtgc aaaagatagg   300
tatggttcgg ggacttatca gttcggtatg gacgtctggg gcccgggaac cctggtcacc   360
gtctcctca                                                           369

<210> SEQ ID NO 23
<211> LENGTH: 369

<212> TYPE: DNA
<213> ORGANISM: Artificial Sequence
<220> FEATURE:
<223> OTHER INFORMATION: #3NNK

<400> SEQUENCE: 23

```
gaggtgcagc tggtggagtc tggggctgag gtgaggaagc ctggggcctc agtgaaggtc    60
tcctgcaagg cttctggata caccttcacc agttctgata tcaactggat tcgacaggcc   120
actggacaag gcttgagtg gatgggatac atgaaccta aaaatggaaa cacagactat    180
gcacagaagt tccagggcag aatctccatg accagggaca gctccataag cacagcctac   240
atggagctga gcagcctgag atctgaggac acggccgtgt attactgtgc aaaagatagg   300
tatggttcgg ggactattgg cttcggtatg gacgtctggg gcccgggaac cctggtcacc   360
gtctcctca                                                          369
```

<210> SEQ ID NO 24
<211> LENGTH: 369
<212> TYPE: DNA
<213> ORGANISM: Artificial Sequence
<220> FEATURE:
<223> OTHER INFORMATION: #4NNK

<400> SEQUENCE: 24

```
gaggtgcagc tggtggagtc tggggctgag gtgaggaagc ctggggcctc agtgaaggtc    60
tcctgcaagg cttctggata caccttcacc agttctgata tcaactggat tcgacaggcc   120
actggacaag gcttgagtg gatgggatac atgaaccta aaaatggaaa cacagactat    180
gcacagaagt tccagggcag aatctccatg accagggaca gctccataag cacagcctac   240
atggagctga gcagcctgag atctgaggac acggccgtgt attactgtgc aaaagatagg   300
tatggttcgg ggactcatgg cttcggtatg gacgtctggg gcccgggaac cctggtcacc   360
gtctcctca                                                          369
```

<210> SEQ ID NO 25
<211> LENGTH: 369
<212> TYPE: DNA
<213> ORGANISM: Artificial Sequence
<220> FEATURE:
<223> OTHER INFORMATION: #5NNK

<400> SEQUENCE: 25

```
gaggtgcagc tggtggagtc tggggctgag gtgaggaagc ctggggcctc agtgaaggtc    60
tcctgcaagg cttctggata caccttcacc agttctgata tcaactggat tcgacaggcc   120
actggacaag gcttgagtg gatgggatac atgaaccta aaaatggaaa cacagactat    180
gcacagaagt tccagggcag aatctccatg accagggaca gctccataag cacagcctac   240
atggagctga gcagcctgag atctgaggac acggccgtgt attactgtgc aaaagatagg   300
tatggttcgg ggacttatgg cttcaatatg gacgtctggg gcccgggaac cctggtcacc   360
gtctcctca                                                          369
```

<210> SEQ ID NO 26
<211> LENGTH: 369
<212> TYPE: DNA
<213> ORGANISM: Artificial Sequence
<220> FEATURE:
<223> OTHER INFORMATION: #6NNK

<400> SEQUENCE: 26

```
gaggtgcagc tggtggagtc tggggctgag gtgaggaagc tggggcctc agtgaaggtc      60 tcctgcaagg cttctggata caccttcacc agttctgata tcaactggat tcgacaggcc     120
actggacaag ggcttgagtg gatgggatac atgaaccta aaaatggaaa cacagactat     180
gcacagaagt tccagggcag aatctccatg accagggaca gctccataag cacagcctac    240
atggagctga gcagcctgag atctgaggac acggccgtgt attactgtgc aaaagatagg    300
tatggttcgg ggacttatgg cttctgtatg gacgtctggg gcccgggaac cctggtcacc    360
gtctcctca                                                             369
```

<210> SEQ ID NO 27
<211> LENGTH: 369
<212> TYPE: DNA
<213> ORGANISM: Artificial Sequence
<220> FEATURE:
<223> OTHER INFORMATION: #7NNK

<400> SEQUENCE: 27

```
gaggtgcagc tggtggagtc tggggctgag gtgaggaagc tggggcctc agtgaaggtc      60 tcctgcaagg cttctggata caccttcacc agttctgata tcaactggat tcgacaggcc     120
actggacaag ggcttgagtg gatgggatac atgaaccta aaaatggaaa cacagactat     180
gcacagaagt tccagggcag aatctccatg accagggaca gctccataag cacagcctac    240
atggagctga gcagcctgag atctgaggac acggccgtgt attactgtgc aaaagatagg    300
tatggttcgg ggacttatgg cttcggtctg gacgtctggg gcccgggaac cctggtcacc    360
gtctcctca                                                             369
```

<210> SEQ ID NO 28
<211> LENGTH: 251
<212> TYPE: PRT
<213> ORGANISM: Artificial Sequence
<220> FEATURE:
<223> OTHER INFORMATION: scFv-AG8

<400> SEQUENCE: 28

```
Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Phe Gly Met Asp Val
            100                 105                 110

Trp Gly Pro Gly Thr Leu Val Thr Val Ser Ser Gly Gly Gly Ser Ser
        115                 120                 125

Gly Gly Gly Gly Ser Gly Gly Gly Ser Gly Gly Gly Gly Ser Asp
    130                 135                 140

Ile Val Met Thr Gln Ser Pro Ser Ala Met Ser Ala Ser Val Gly Asp
145                 150                 155                 160

Arg Val Ser Ile Thr Cys Arg Ala Ser Gln Gly Ile Asn Asn Tyr Leu
```

```
                    165                 170                 175

Ala Trp Phe Gln Gln Lys Pro Gly Lys Val Pro Lys Arg Leu Met Asp
                180                 185                 190

Val Gly Ser Ile Leu Gln Ser Gly Ile Pro Ser Arg Phe Arg Gly Arg
                195                 200                 205

Gly Ser Gly Thr Gln Phe Thr Leu Thr Ile Ser Ser Leu Gln Ala Glu
                210                 215                 220

Asp Ser Gly Thr Tyr Phe Cys Leu Gln His Asn Thr Tyr Pro Leu Thr
225                 230                 235                 240

Phe Gly Pro Gly Thr Lys Val Glu Ile Lys Arg
                245                 250

<210> SEQ ID NO 29
<211> LENGTH: 251
<212> TYPE: PRT
<213> ORGANISM: Artificial Sequence
<220> FEATURE:
<223> OTHER INFORMATION: scFv-EF12

<400> SEQUENCE: 29

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
            35                  40                  45

Gly Tyr Met Asn Pro Lys Asn Gly Asn Thr Asp Tyr Ala Gln Lys Phe
        50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Pro Tyr Gly Ser Gly Thr Tyr Gly Phe Gly Met Asp Val
                100                 105                 110

Trp Gly Pro Gly Thr Leu Val Thr Val Ser Ser Gly Gly Gly Ser Ser
                115                 120                 125

Gly Gly Gly Gly Ser Gly Gly Gly Ser Gly Gly Gly Ser Asp
            130                 135                 140

Ile Val Met Thr Gln Ser Pro Ser Ala Met Ser Ala Ser Val Gly Asp
145                 150                 155                 160

Arg Val Ser Ile Thr Cys Arg Ala Ser Gln Gly Ile Asn Asn Tyr Leu
                165                 170                 175

Ala Trp Phe Gln Gln Lys Pro Gly Lys Val Pro Lys Arg Leu Met Asp
                180                 185                 190

Val Gly Ser Ile Leu Gln Ser Gly Ile Pro Ser Arg Phe Arg Gly Arg
                195                 200                 205

Gly Ser Gly Thr Gln Phe Thr Leu Thr Ile Ser Ser Leu Gln Ala Glu
                210                 215                 220

Asp Ser Gly Thr Tyr Phe Cys Leu Gln His Asn Thr Tyr Pro Leu Thr
225                 230                 235                 240

Phe Gly Pro Gly Thr Lys Val Glu Ile Lys Arg
                245                 250

<210> SEQ ID NO 30
<211> LENGTH: 251
<212> TYPE: PRT
```

<213> ORGANISM: Artificial Sequence
<220> FEATURE:
<223> OTHER INFORMATION: scFv-GG12

<400> SEQUENCE: 30

| | | | | | | | | | | | | | | |
|---|---|---|---|---|---|---|---|---|---|---|---|---|---|---|
| Glu | Val | Gln | Leu | Val | Glu | Ser | Gly | Ala | Glu | Val | Arg | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Ser |
| | | | 20 | | | | | 25 | | | | | 30 | | |
| Asp | Ile | Asn | Trp | Ile | Arg | Gln | Ala | Thr | Gly | Gln | Gly | Leu | Glu | Trp | Met |
| | | 35 | | | | | 40 | | | | | 45 | | | |
| Gly | Tyr | Met | Asn | Pro | Lys | Asn | Gly | Asn | Thr | Asp | Tyr | Ala | Gln | Lys | Phe |
| | 50 | | | | | 55 | | | | | 60 | | | | |
| Gln | Gly | Arg | Ile | Ser | Met | Thr | Arg | Asp | Ser | Ser | Ile | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Lys | Asp | Arg | Tyr | Gly | Ser | Gly | Val | Tyr | Gly | Phe | Gly | Met | Asp | Val |
| | | | 100 | | | | | 105 | | | | | 110 | | |
| Trp | Gly | Pro | Gly | Thr | Leu | Val | Thr | Val | Ser | Ser | Gly | Gly | Gly | Ser | Ser |
| | | 115 | | | | | 120 | | | | | 125 | | | |
| Gly | Gly | Gly | Gly | Ser | Gly | Gly | Gly | Ser | Gly | Gly | Gly | Ser | Asp |
| | 130 | | | | | 135 | | | | | 140 | | | | |
| Ile | Val | Met | Thr | Gln | Ser | Pro | Ser | Ala | Met | Ser | Ala | Ser | Val | Gly | Asp |
| 145 | | | | | 150 | | | | | 155 | | | | | 160 |
| Arg | Val | Ser | Ile | Thr | Cys | Arg | Ala | Ser | Gln | Gly | Ile | Asn | Asn | Tyr | Leu |
| | | | | 165 | | | | | 170 | | | | | 175 | |
| Ala | Trp | Phe | Gln | Gln | Lys | Pro | Gly | Lys | Val | Pro | Lys | Arg | Leu | Met | Asp |
| | | | 180 | | | | | 185 | | | | | 190 | | |
| Val | Gly | Ser | Ile | Leu | Gln | Ser | Gly | Ile | Pro | Ser | Arg | Phe | Arg | Gly | Arg |
| | | 195 | | | | | 200 | | | | | 205 | | | |
| Gly | Ser | Gly | Thr | Gln | Phe | Thr | Leu | Thr | Ile | Ser | Ser | Leu | Gln | Ala | Glu |
| | 210 | | | | | 215 | | | | | 220 | | | | |
| Asp | Ser | Gly | Thr | Tyr | Phe | Cys | Leu | Gln | His | Asn | Thr | Tyr | Pro | Leu | Thr |
| 225 | | | | | 230 | | | | | 235 | | | | | 240 |
| Phe | Gly | Pro | Gly | Thr | Lys | Val | Glu | Ile | Lys | Arg | | | | | |
| | | | | 245 | | | | | 250 | | | | | | |

<210> SEQ ID NO 31
<211> LENGTH: 251
<212> TYPE: PRT
<213> ORGANISM: Artificial Sequence
<220> FEATURE:
<223> OTHER INFORMATION: scFv-FG12

<400> SEQUENCE: 31

| | | | | | | | | | | | | | | | |
|---|---|---|---|---|---|---|---|---|---|---|---|---|---|---|---|
| Glu | Val | Gln | Leu | Val | Glu | Ser | Gly | Ala | Glu | Val | Arg | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Ser |
| | | | 20 | | | | | 25 | | | | | 30 | | |
| Asp | Ile | Asn | Trp | Ile | Arg | Gln | Ala | Thr | Gly | Gln | Gly | Leu | Glu | Trp | Met |
| | | 35 | | | | | 40 | | | | | 45 | | | |
| Gly | Tyr | Met | Asn | Pro | Lys | Asn | Gly | Asn | Thr | Asp | Tyr | Ala | Gln | Lys | Phe |
| | 50 | | | | | 55 | | | | | 60 | | | | |
| Gln | Gly | Arg | Ile | Ser | Met | Thr | Arg | Asp | Ser | Ser | Ile | Ser | Thr | Ala | Tyr |
| 65 | | | | | 70 | | | | | 75 | | | | | 80 |

```
Met Glu Leu Ser Ser Leu Arg Ser Glu Asp Thr Ala Val Tyr Tyr Cys
                85                  90                  95

Ala Lys Asp Arg Tyr Gly Leu Gly Thr Tyr Gly Phe Gly Met Asp Val
            100                 105                 110

Trp Gly Pro Gly Thr Leu Val Thr Val Ser Ser Gly Gly Gly Ser Ser
            115                 120                 125

Gly Gly Gly Gly Ser Gly Gly Gly Ser Gly Gly Gly Ser Asp
            130                 135                 140

Ile Val Met Thr Gln Ser Pro Ser Ala Met Ser Ala Ser Val Gly Asp
145                 150                 155                 160

Arg Val Ser Ile Thr Cys Arg Ala Ser Gln Gly Ile Asn Asn Tyr Leu
                165                 170                 175

Ala Trp Phe Gln Gln Lys Pro Gly Lys Val Pro Lys Arg Leu Met Asp
            180                 185                 190

Val Gly Ser Ile Leu Gln Ser Gly Ile Pro Ser Arg Phe Arg Gly Arg
            195                 200                 205

Gly Ser Gly Thr Gln Phe Thr Leu Thr Ile Ser Ser Leu Gln Ala Glu
            210                 215                 220

Asp Ser Gly Thr Tyr Phe Cys Leu Gln His Asn Thr Tyr Pro Leu Thr
225                 230                 235                 240

Phe Gly Pro Gly Thr Lys Val Glu Ile Lys Arg
                245                 250

<210> SEQ ID NO 32
<211> LENGTH: 251
<212> TYPE: PRT
<213> ORGANISM: Artificial Sequence
<220> FEATURE:
<223> OTHER INFORMATION: scFv-AB9

<400> SEQUENCE: 32

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
            35                  40                  45

Gly Tyr Met Asn Pro Lys Asn Gly Asn Thr Asp Tyr Ala Gln Lys Phe
50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Glu Gly Met Asp Val
            100                 105                 110

Trp Gly Pro Gly Thr Leu Val Thr Val Ser Ser Gly Gly Gly Ser Ser
            115                 120                 125

Gly Gly Gly Gly Ser Gly Gly Gly Ser Gly Gly Gly Ser Asp
            130                 135                 140

Ile Val Met Thr Gln Ser Pro Ser Ala Met Ser Ala Ser Val Gly Asp
145                 150                 155                 160

Arg Val Ser Ile Thr Cys Arg Ala Ser Gln Gly Ile Asn Asn Tyr Leu
                165                 170                 175

Ala Trp Phe Gln Gln Lys Pro Gly Lys Val Pro Lys Arg Leu Met Asp
            180                 185                 190
```

```
Val Gly Ser Ile Leu Gln Ser Gly Ile Pro Ser Arg Phe Arg Gly Arg
            195                 200                 205

Gly Ser Gly Thr Gln Phe Thr Leu Thr Ile Ser Ser Leu Gln Ala Glu
        210                 215                 220

Asp Ser Gly Thr Tyr Phe Cys Leu Gln His Asn Thr Tyr Pro Leu Thr
225                 230                 235                 240

Phe Gly Pro Gly Thr Lys Val Glu Ile Lys Arg
                245                 250

<210> SEQ ID NO 33
<211> LENGTH: 753
<212> TYPE: DNA
<213> ORGANISM: Artificial Sequence
<220> FEATURE:
<223> OTHER INFORMATION: scFv-AG8

<400> SEQUENCE: 33
gaggtgcagc tggtggagtc tggggctgag gtgaggaagc ctggggcctc agtgaaggtc      60
tcctgcaagg cttctggata caccttcacc agttctgata tcaactggat tcgacaggcc    120
actggacaag ggcttgagtg gatgggatac atgaaccota aaatggaaaa cacagactat    180
gcacagaagt tccagggcag aatctccatg accaggaca gctccataag cacagcctac     240
atggagctga gcagcctgag atctgaggac acggccgtgt attactgtgc aaaagatagg    300
tatggttcgg ggacttatgg cttcggtatg gacgtctggg gcccgggaac cctggtcacc    360
gtctcctcag gtgagggag ctctggaggt ggaggttccg gtggaggtgg atctggtgga     420
ggtggaagtg acatcgtgat gacccagtct ccatctgcca tgtctgcatc tgtcggagac    480
agagtctcca tcacttgtcg ggcgagtcag ggcattaaca attatttagc ctggtttcag    540
cagaaaccag gaaagtccc taagcgcctg atggatgttg gatccatttt gcaaagtggc    600
atcccatcaa gattcagggg cagaggctct gggacacaat tcactctcac aatcagcagc    660
ctgcaggcag aagattcagg cacttatttc tgtcttcagc ataatactta ccccctcact    720
ttcggccctg gaccaaggt ggagatcaaa cgt                                  753

<210> SEQ ID NO 34
<211> LENGTH: 753
<212> TYPE: DNA
<213> ORGANISM: Artificial Sequence
<220> FEATURE:
<223> OTHER INFORMATION: scFv-EF12

<400> SEQUENCE: 34
gaggtgcagc tggtggagtc tggggctgag gtgaggaagc ctggggcctc agtgaaggtc      60
tcctgcaagg cttctggata caccttcacc agttctgata tcaactggat tcgacaggcc    120
actggacaag ggcttgagtg gatgggatac atgaaccota aaatggaaaa cacagactat    180
gcacagaagt tccagggcag aatctccatg accaggaca gctccataag cacagcctac     240
atggagctga gcagcctgag atctgaggac acggccgtgt attactgtgc aaaagatccg    300
tatggttcgg ggacttatgg cttcggtatg gacgtctggg gcccgggaac cctggtcacc    360
gtctcctcag gtgagggag ctctggaggt ggaggttccg gtggaggtgg atctggtgga     420
ggtggaagtg acatcgtgat gacccagtct ccatctgcca tgtctgcatc tgtcggagac    480
agagtctcca tcacttgtcg ggcgagtcag ggcattaaca attatttagc ctggtttcag    540
cagaaaccag gaaagtccc taagcgcctg atggatgttg gatccatttt gcaaagtggc    600
atcccatcaa gattcagggg cagaggctct gggacacaat tcactctcac aatcagcagc    660
```

| ctgcaggcag aagattcagg cacttatttc tgtcttcagc ataatactta ccccctcact | 720 |
| ttcggccctg ggaccaaggt ggagatcaaa cgt | 753 |

<210> SEQ ID NO 35
<211> LENGTH: 753
<212> TYPE: DNA
<213> ORGANISM: Artificial Sequence
<220> FEATURE:
<223> OTHER INFORMATION: scFv-GG12

<400> SEQUENCE: 35

| gaggtgcagc tggtggagtc tggggctgag gtgaggaagc ctggggcctc agtgaaggtc | 60 |
| tcctgcaagg cttctggata caccttcacc agttctgata tcaactggat tcgacaggcc | 120 |
| actggacaag gcttgagtg gatgggatac atgaacccta aaaatggaaa cacagactat | 180 |
| gcacagaagt tccagggcag aatctccatg accagggaca gctccataag cacagcctac | 240 |
| atggagctga gcagcctgag atctgaggac acggccgtgt attactgtgc aaaagatagg | 300 |
| tatggttcgg gggtgtatgg cttcggtatg gacgtctggg gccgggaac cctggtcacc | 360 |
| gtctcctcag gtggagggag ctctggaggt ggaggttccg gtggaggtgg atctggtgga | 420 |
| ggtggaagtg acatcgtgat gacccagtct ccatctgcca tgtctgcatc tgtcggagac | 480 |
| agagtctcca tcacttgtcg ggcgagtcag ggcattaaca attatttagc ctggtttcag | 540 |
| cagaaaccag ggaaagtccc taagcgcctg atggatgttg gatccatttt gcaaagtggc | 600 |
| atcccatcaa gattcagggg cagaggctct gggacacaat tcactctcac aatcagcagc | 660 |
| ctgcaggcag aagattcagg cacttatttc tgtcttcagc ataatactta ccccctcact | 720 |
| ttcggccctg ggaccaaggt ggagatcaaa cgt | 753 |

<210> SEQ ID NO 36
<211> LENGTH: 753
<212> TYPE: DNA
<213> ORGANISM: Artificial Sequence
<220> FEATURE:
<223> OTHER INFORMATION: scFv-FG12

<400> SEQUENCE: 36

| gaggtgcagc tggtggagtc tggggctgag gtgaggaagc ctggggcctc agtgaaggtc | 60 |
| tcctgcaagg cttctggata caccttcacc agttctgata tcaactggat acgacaggcc | 120 |
| actggacaag gcttgagtg gatgggatac atgaacccta aaaatggaaa cacagactat | 180 |
| gcacagaagt tccagggcag aatctccatg accagggaca gctccataag cacagcctac | 240 |
| atggagctga gcagcctgag atctgaggac acggccgtgt attactgtgc aaaagatagg | 300 |
| tatggtcttg ggacttatgg cttcggtatg gacgtctggg gccgggaac cctggtcacc | 360 |
| gtctcctcag gtggagggag ctctggaggt ggaggttccg gtggaggtgg atctggtgga | 420 |
| ggtggaagtg acatcgtgat gacccagtct ccatctgcca tgtctgcatc tgtcggagac | 480 |
| agagtctcca tcacttgtcg ggcgagtcag ggcattaaca attatttagc ctggtttcag | 540 |
| cagaaaccag ggaaagtccc taagcgcctg atggatgttg gatccatttt gcaaagtggc | 600 |
| atcccatcaa gattcagggg cagaggctct gggacacaat tcactctcac aatcagcagc | 660 |
| ctgcaggcag aagattcagg cacttatttc tgtcttcagc ataatactta ccccctcact | 720 |
| ttcggccctg ggaccaaggt ggagatcaaa cgt | 753 |

<210> SEQ ID NO 37

<211> LENGTH: 753
<212> TYPE: DNA
<213> ORGANISM: Artificial Sequence
<220> FEATURE:
<223> OTHER INFORMATION: scFv-AB9

<400> SEQUENCE: 37

```
gaggtgcagc tggtggagtc tggggctgag gtgaggaagc ctggggcctc agtgaaggtc    60
tcctgcaagg cttctggata caccttcacc agttctgata tcaactggat tcgacaggcc   120
actggacaag gcttgagtg atgggatac atgaaccta aaaatggaaa cacagactat   180
gcacagaagt tccagggcag aatctccatg accagggaca gctccataag cacagcctac   240
atggagctga gcagcctgag atctgaggac acggccgtgt attactgtgc aaaagatagg   300
tatggttcgg ggacttatgg cgagggtatg gacgtctggg gcccgggaac cctggtcacc   360
gtctcctcag gtggagggag ctctggaggt ggaggttccg gtggaggtgg atctggtgga   420
ggtggaagtg acatcgtgat gacccagtct ccatctgcca tgtctgcatc tgtcggagac   480
agagtctcca tcacttgtcg ggcgagtcag ggcattaaca attatttagc ctggtttcag   540
cagaaaccag ggaaagtccc taagcgcctg atggatgttg gatccatttt gcaaagtggc   600
atcccatcaa gattcagggg cagaggctct gggacacaat tcactctcac aatcagcagc   660
ctgcaggcag aagattcagg cacttatttc tgtcttcagc ataatactta ccccctcact   720
ttcggccctg ggaccaaggt ggagatcaaa cgt                                753
```

<210> SEQ ID NO 38
<211> LENGTH: 7
<212> TYPE: PRT
<213> ORGANISM: Artificial Sequence
<220> FEATURE:
<223> OTHER INFORMATION: HCDR1

<400> SEQUENCE: 38

Gly Tyr Thr Phe Thr Ser Ser
1               5

<210> SEQ ID NO 39
<211> LENGTH: 8
<212> TYPE: PRT
<213> ORGANISM: Artificial Sequence
<220> FEATURE:
<223> OTHER INFORMATION: HCDR2

<400> SEQUENCE: 39

Met Asn Pro Lys Asn Gly Asn Thr
1               5

<210> SEQ ID NO 40
<211> LENGTH: 6
<212> TYPE: PRT
<213> ORGANISM: Artificial Sequence
<220> FEATURE:
<223> OTHER INFORMATION: LCDR1

<400> SEQUENCE: 40

Gln Gly Ile Asn Asn Tyr
1               5

<210> SEQ ID NO 41
<211> LENGTH: 3
<212> TYPE: PRT
<213> ORGANISM: Artificial Sequence
<220> FEATURE:

```
<223> OTHER INFORMATION: LCDR2

<400> SEQUENCE: 41

Val Gly Ser
1

<210> SEQ ID NO 42
<211> LENGTH: 9
<212> TYPE: PRT
<213> ORGANISM: Artificial Sequence
<220> FEATURE:
<223> OTHER INFORMATION: LCDR3

<400> SEQUENCE: 42

Leu Gln His Asn Thr Tyr Pro Leu Thr
1               5

<210> SEQ ID NO 43
<211> LENGTH: 16
<212> TYPE: PRT
<213> ORGANISM: Artificial Sequence
<220> FEATURE:
<223> OTHER INFORMATION: HCDR3-AG8

<400> SEQUENCE: 43

Ala Lys Asp Arg Tyr Gly Ser Gly Thr Tyr Gly Phe Gly Met Asp Val
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: HCDR3-#1NNK

<400> SEQUENCE: 44

Ala Lys Asp Arg Tyr Gly Ser Gly Thr Tyr Phe Phe Gly Met Asp Val
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: HCDR3-#2NNK

<400> SEQUENCE: 45

Ala Lys Asp Arg Tyr Gly Ser Gly Thr Tyr Gln Phe Gly Met Asp Val
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: HCDR3-#3NNK

<400> SEQUENCE: 46

Ala Lys Asp Arg Tyr Gly Ser Gly Thr Ile Gly Phe Gly Met Asp Val
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: HCDR3-#4NNK
```

```
<400> SEQUENCE: 47

Ala Lys Asp Arg Tyr Gly Ser Gly Thr His Gly Phe Gly Met Asp Val
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: HCDR3-#5NNK

<400> SEQUENCE: 48

Ala Lys Asp Arg Tyr Gly Ser Gly Thr Tyr Gly Phe Asn Met Asp Val
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: HCDR3-#6NNK

<400> SEQUENCE: 49

Ala Lys Asp Arg Tyr Gly Ser Gly Thr Tyr Gly Phe Cys Met Asp Val
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: HCDR3-#7NNK

<400> SEQUENCE: 50

Ala Lys Asp Arg Tyr Gly Ser Gly Thr Tyr Gly Phe Gly Leu Asp Val
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: HCDR3-EF12

<400> SEQUENCE: 51

Ala Lys Asp Pro Tyr Gly Ser Gly Thr Tyr Gly Phe Gly Met Asp Val
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: HCDR3-GG12

<400> SEQUENCE: 52

Ala Lys Asp Arg Tyr Gly Ser Gly Val Tyr Gly Phe Gly Met Asp Val
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: HCDR3-FG12
```

<400> SEQUENCE: 53

Ala Lys Asp Arg Tyr Gly Leu Gly Thr Tyr Gly Phe Gly Met Asp Val
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: HCDR3-AB9

<400> SEQUENCE: 54

Ala Lys Asp Arg Tyr Gly Ser Gly Thr Tyr Gly Glu Gly Met Asp Val
1               5                   10                  15

<210> SEQ ID NO 55
<211> LENGTH: 108
<212> TYPE: PRT
<213> ORGANISM: Artificial Sequence
<220> FEATURE:
<223> OTHER INFORMATION: VL

<400> SEQUENCE: 55

Asp Ile Val Met Thr Gln Ser Pro Ser Ala Met Ser Ala Ser Val Gly
1               5                   10                  15

Asp Arg Val Ser Ile Thr Cys Arg Ala Ser Gln Gly Ile Asn Asn Tyr
                20                  25                  30

Leu Ala Trp Phe Gln Gln Lys Pro Gly Lys Val Pro Lys Arg Leu Met
            35                  40                  45

Asp Val Gly Ser Ile Leu Gln Ser Gly Ile Pro Ser Arg Phe Arg Gly
        50                  55                  60

Arg Gly Ser Gly Thr Gln Phe Thr Leu Thr Ile Ser Ser Leu Gln Ala
65                  70                  75                  80

Glu Asp Ser Gly Thr Tyr Phe Cys Leu Gln His Asn Thr Tyr Pro Leu
                85                  90                  95

Thr Phe Gly Pro Gly Thr Lys Val Glu Ile Lys Arg
            100                 105

<210> SEQ ID NO 56
<211> LENGTH: 120
<212> TYPE: PRT
<213> ORGANISM: Artificial Sequence
<220> FEATURE:
<223> OTHER INFORMATION: VH-AG8

<400> SEQUENCE: 56

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
            35                  40                  45

Gly Tyr Met Asn Pro Lys Asn Gly Asn Thr Asp Tyr Ala Gln Lys Phe
        50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Phe Gly Met Asp Val
            100                 105                 110

```
Trp Gly Pro Gly Thr Leu Val Thr
        115                 120

<210> SEQ ID NO 57
<211> LENGTH: 120
<212> TYPE: PRT
<213> ORGANISM: Artificial Sequence
<220> FEATURE:
<223> OTHER INFORMATION: VH-#1NNK

<400> SEQUENCE: 57

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Phe Phe Gly Met Asp Val
            100                 105                 110

Trp Gly Pro Gly Thr Leu Val Thr
        115                 120

<210> SEQ ID NO 58
<211> LENGTH: 120
<212> TYPE: PRT
<213> ORGANISM: Artificial Sequence
<220> FEATURE:
<223> OTHER INFORMATION: VH-#2NNK

<400> SEQUENCE: 58

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Met Arg Ser Glu Asp Thr Ala Val Tyr Tyr Cys
                85                  90                  95

Ala Lys Asp Arg Tyr Gly Ser Gly Thr Tyr Gln Phe Gly Met Asp Val
            100                 105                 110

Trp Gly Pro Gly Thr Leu Val Thr
        115                 120

<210> SEQ ID NO 59
<211> LENGTH: 120
<212> TYPE: PRT
<213> ORGANISM: Artificial Sequence
<220> FEATURE:
<223> OTHER INFORMATION: VH-#3NNK
```

<400> SEQUENCE: 59

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Ile Gly Phe Gly Met Asp Val
            100                 105                 110

Trp Gly Pro Gly Thr Leu Val Thr
            115                 120

<210> SEQ ID NO 60
<211> LENGTH: 120
<212> TYPE: PRT
<213> ORGANISM: Artificial Sequence
<220> FEATURE:
<223> OTHER INFORMATION: VH-#4NNK

<400> SEQUENCE: 60

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr His Gly Phe Gly Met Asp Val
            100                 105                 110

Trp Gly Pro Gly Thr Leu Val Thr
            115                 120

<210> SEQ ID NO 61
<211> LENGTH: 120
<212> TYPE: PRT
<213> ORGANISM: Artificial Sequence
<220> FEATURE:
<223> OTHER INFORMATION: VH-#5NNK

<400> SEQUENCE: 61

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
          50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Phe Asn Met Asp Val
            100                 105                 110

Trp Gly Pro Gly Thr Leu Val Thr
            115                 120

<210> SEQ ID NO 62
<211> LENGTH: 120
<212> TYPE: PRT
<213> ORGANISM: Artificial Sequence
<220> FEATURE:
<223> OTHER INFORMATION: VH-#6NNK

<400> SEQUENCE: 62

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
            35                  40                  45

Gly Tyr Met Asn Pro Lys Asn Gly Asn Thr Asp Tyr Ala Gln Lys Phe
          50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Phe Cys Met Asp Val
            100                 105                 110

Trp Gly Pro Gly Thr Leu Val Thr
            115                 120

<210> SEQ ID NO 63
<211> LENGTH: 120
<212> TYPE: PRT
<213> ORGANISM: Artificial Sequence
<220> FEATURE:
<223> OTHER INFORMATION: VH-#7NNK

<400> SEQUENCE: 63

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
            35                  40                  45

Gly Tyr Met Asn Pro Lys Asn Gly Asn Thr Asp Tyr Ala Gln Lys Phe
          50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Phe Gly Leu Asp Val

Trp Gly Pro Gly Thr Leu Val Thr
        115                 120

<210> SEQ ID NO 64
<211> LENGTH: 120
<212> TYPE: PRT
<213> ORGANISM: Artificial Sequence
<220> FEATURE:
<223> OTHER INFORMATION: VH-EF12

<400> SEQUENCE: 64

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
            35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Pro Tyr Gly Ser Gly Thr Tyr Gly Phe Gly Met Asp Val
                100                 105                 110

Trp Gly Pro Gly Thr Leu Val Thr
        115                 120

<210> SEQ ID NO 65
<211> LENGTH: 120
<212> TYPE: PRT
<213> ORGANISM: Artificial Sequence
<220> FEATURE:
<223> OTHER INFORMATION: VH-GG12

<400> SEQUENCE: 65

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
                20                  25                  30

Asp Ile Asn Trp Ile Arg Gln Ala Thr Gly Gln Gly Leu Glu Trp Met
            35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Val Tyr Gly Phe Gly Met Asp Val
                100                 105                 110

Trp Gly Pro Gly Thr Leu Val Thr
        115                 120

<210> SEQ ID NO 66
<211> LENGTH: 120
<212> TYPE: PRT
<213> ORGANISM: Artificial Sequence
<220> FEATURE:

<223> OTHER INFORMATION: VH-FG12

<400> SEQUENCE: 66

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Leu Gly Thr Tyr Gly Phe Gly Met Asp Val
            100                 105                 110

Trp Gly Pro Gly Thr Leu Val Thr
        115                 120

<210> SEQ ID NO 67
<211> LENGTH: 120
<212> TYPE: PRT
<213> ORGANISM: Artificial Sequence
<220> FEATURE:
<223> OTHER INFORMATION: VH-AB9

<400> SEQUENCE: 67

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Glu Gly Met Asp Val
            100                 105                 110

Trp Gly Pro Gly Thr Leu Val Thr
        115                 120

<210> SEQ ID NO 68
<211> LENGTH: 407
<212> TYPE: PRT
<213> ORGANISM: Artificial Sequence
<220> FEATURE:
<223> OTHER INFORMATION: Endothelin receptor type A

<400> SEQUENCE: 68

Asp Asn Pro Glu Arg Tyr Ser Thr Asn Leu Ser Asn His Val Asp Asp
1               5                   10                  15

Phe Thr Thr Phe Arg Gly Thr Glu Leu Ser Phe Leu Val Thr Thr His
            20                  25                  30

Gln Pro Thr Asn Leu Val Leu Pro Ser Asn Gly Ser Met His Asn Tyr

```
            35                  40                  45
Cys Pro Gln Gln Thr Lys Ile Thr Ser Ala Phe Lys Tyr Ile Asn Thr
 50                  55                  60

Val Ile Ser Cys Thr Ile Phe Ile Val Gly Met Val Gly Asn Ala Thr
 65                  70                  75                  80

Leu Leu Arg Ile Ile Tyr Gln Asn Lys Cys Met Arg Asn Gly Pro Asn
                 85                  90                  95

Ala Leu Ile Ala Ser Leu Ala Leu Gly Asp Leu Ile Tyr Val Val Ile
                100                 105                 110

Asp Leu Pro Ile Asn Val Phe Lys Leu Leu Ala Gly Arg Trp Pro Phe
                115                 120                 125

Asp His Asn Asp Phe Gly Val Phe Leu Cys Lys Leu Phe Pro Phe Leu
                130                 135                 140

Gln Lys Ser Ser Val Gly Ile Thr Val Leu Asn Leu Cys Ala Leu Ser
145                 150                 155                 160

Val Asp Arg Tyr Arg Ala Val Ala Ser Trp Ser Arg Val Gln Gly Ile
                165                 170                 175

Gly Ile Pro Leu Val Thr Ala Ile Glu Ile Val Ser Ile Trp Ile Leu
                180                 185                 190

Ser Phe Ile Leu Ala Ile Pro Glu Ala Ile Gly Phe Val Met Val Pro
                195                 200                 205

Phe Glu Tyr Arg Gly Glu Gln His Lys Thr Cys Met Leu Asn Ala Thr
210                 215                 220

Ser Lys Phe Met Glu Phe Tyr Gln Asp Val Lys Asp Trp Trp Leu Phe
225                 230                 235                 240

Gly Phe Tyr Phe Cys Met Pro Leu Val Cys Thr Ala Ile Phe Tyr Thr
                245                 250                 255

Leu Met Thr Cys Glu Met Leu Asn Arg Arg Asn Gly Ser Leu Arg Ile
                260                 265                 270

Ala Leu Ser Glu His Leu Lys Gln Arg Arg Glu Val Ala Lys Thr Val
                275                 280                 285

Phe Cys Leu Val Val Ile Phe Ala Leu Cys Trp Phe Pro Leu His Leu
290                 295                 300

Ser Arg Ile Leu Lys Lys Thr Val Tyr Asn Glu Met Asp Lys Asn Arg
305                 310                 315                 320

Cys Glu Leu Leu Ser Phe Leu Leu Met Asp Tyr Ile Gly Ile Asn
                325                 330                 335

Leu Ala Thr Met Asn Ser Cys Ile Asn Pro Ile Ala Leu Tyr Phe Val
                340                 345                 350

Ser Lys Lys Phe Lys Asn Cys Phe Gln Ser Cys Leu Cys Cys Cys Cys
                355                 360                 365

Tyr Gln Ser Lys Ser Leu Met Thr Ser Val Pro Met Asn Gly Thr Ser
                370                 375                 380

Ile Gln Trp Lys Asn His Asp Gln Asn Asn His Asn Thr Asp Arg Ser
385                 390                 395                 400

Ser His Lys Asp Ser Met Asn
                405

<210> SEQ ID NO 69
<211> LENGTH: 49
<212> TYPE: PRT
<213> ORGANISM: Artificial Sequence
<220> FEATURE:
<223> OTHER INFORMATION: ETA receptor - N-term
```

<400> SEQUENCE: 69

Asp Asn Pro Glu Arg Tyr Ser Thr Asn Leu Ser Asn His Val Asp Asp
1               5                   10                  15

Phe Thr Thr Phe Arg Gly Thr Glu Leu Ser Phe Leu Val Thr Thr His
            20                  25                  30

Gln Pro Thr Asn Leu Val Leu Pro Ser Asn Gly Ser Met His Asn Tyr
        35                  40                  45

Cys

<210> SEQ ID NO 70
<211> LENGTH: 13
<212> TYPE: PRT
<213> ORGANISM: Artificial Sequence
<220> FEATURE:
<223> OTHER INFORMATION: ETA receptor - ECL1

<400> SEQUENCE: 70

Lys Leu Leu Ala Gly Arg Trp Pro Phe Asp His Asn Asp
1               5                   10

<210> SEQ ID NO 71
<211> LENGTH: 22
<212> TYPE: PRT
<213> ORGANISM: Artificial Sequence
<220> FEATURE:
<223> OTHER INFORMATION: ETA receptor - ECL2

<400> SEQUENCE: 71

Phe Val Met Val Pro Phe Glu Tyr Arg Gly Glu Gln His Lys Thr Cys
1               5                   10                  15

Met Leu Asn Ala Thr Ser
            20

<210> SEQ ID NO 72
<211> LENGTH: 16
<212> TYPE: PRT
<213> ORGANISM: Artificial Sequence
<220> FEATURE:
<223> OTHER INFORMATION: ETA receptor - ECL3

<400> SEQUENCE: 72

Lys Thr Val Tyr Asn Glu Met Asp Lys Asn Arg Cys Glu Leu Leu Ser
1               5                   10                  15

<210> SEQ ID NO 73
<211> LENGTH: 123
<212> TYPE: PRT
<213> ORGANISM: Artificial Sequence
<220> FEATURE:
<223> OTHER INFORMATION: AG8 Hc

<400> SEQUENCE: 73

Glu Val Gln Leu Val Glu Ser Gly Ala Glu Val Arg Lys Pro Gly Ala
1               5                   10                  15

Ser Val Lys Val Ser Cys Lys Ala Ser Gly Tyr Thr Phe Thr Ser Ser
            20                  25                  30

Asp Ile Asn Trp Ile Arg Gln Ala Thr Gly Gln Gly Leu Glu Trp Met
        35                  40                  45

Gly Tyr Met Asn Pro Lys Asn Gly Asn Thr Asp Tyr Ala Gln Lys Phe
    50                  55                  60

Gln Gly Arg Ile Ser Met Thr Arg Asp Ser Ser Ile Ser Thr Ala Tyr
65                  70                  75                  80

-continued

```
Met Glu Leu Ser Ser Leu Arg Ser Glu Asp Thr Ala Val Tyr Tyr Cys
                85                  90                  95

Ala Lys Asp Arg Tyr Gly Ser Gly Thr Tyr Gly Phe Gly Met Asp Val
            100                 105                 110

Trp Gly Pro Gly Thr Leu Val Thr Val Ser Ser
        115                 120
```